(12) United States Patent
Clubb et al.

(10) Patent No.: US 8,409,242 B2
(45) Date of Patent: Apr. 2, 2013

(54) EMBOLIC FILTERS WITH CONTROLLED PORE SIZE

(75) Inventors: Thomas L. Clubb, Hudson, WI (US); Richard S. Kusleika, Eden Prairie, MN (US); Kent D. Anderson, Champlin, MN (US); Marwane S. Berrada, Montreal (CA)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/169,229

(22) Filed: Jun. 27, 2011

(65) Prior Publication Data

US 2011/0257676 A1 Oct. 20, 2011

Related U.S. Application Data

(63) Continuation of application No. 11/704,076, filed on Feb. 8, 2007, now abandoned, which is a continuation of application No. 10/354,679, filed on Jan. 30, 2003, now Pat. No. 7,323,001.

(51) Int. Cl.
*A61M 29/00* (2006.01)

(52) U.S. Cl. ................ 606/200; 604/96.01

(58) Field of Classification Search ........... 606/127, 606/159, 200; 604/96.01, 101, 264, 280
See application file for complete search history.

(56) References Cited

U.S. PATENT DOCUMENTS

| | | | |
|---|---|---|---|
| 3,690,606 A * | 9/1972 | Pall | 428/605 |
| 4,425,908 A | 1/1984 | Simon | |
| 4,619,246 A | 10/1986 | Molgaard-Nielsen et al. | |
| 4,640,778 A * | 2/1987 | Blomback et al. | 210/484 |
| 4,789,410 A | 12/1988 | Parizek | |
| 4,864,329 A | 9/1989 | Kneezel et al. | |
| 5,188,734 A | 2/1993 | Zepf | |
| 5,814,064 A | 9/1998 | Daniel et al. | |
| 5,855,598 A | 1/1999 | Pinchuk | |
| 5,901,775 A | 5/1999 | Musschoot et al. | |
| 5,919,224 A | 7/1999 | Thompson et al. | |
| 6,001,118 A | 12/1999 | Daniel et al. | |
| 6,019,784 A | 2/2000 | Hines | |
| 6,053,932 A | 4/2000 | Daniel et al. | |
| 6,059,814 A | 5/2000 | Ladd | |
| 6,066,149 A | 5/2000 | Samson et al. | |
| 6,123,715 A | 9/2000 | Amplatz | |
| 6,129,739 A | 10/2000 | Khosravi | |
| 6,179,859 B1 | 1/2001 | Bates et al. | |
| 6,179,861 B1 | 1/2001 | Khosravi et al. | |
| 6,203,732 B1 | 3/2001 | Clubb et al. | |
| 6,206,868 B1 | 3/2001 | Parodi | |

(Continued)

FOREIGN PATENT DOCUMENTS

| | | |
|---|---|---|
| EP | 0 350 043 A1 | 1/1990 |
| EP | 0 350 043 B1 | 1/1990 |

(Continued)

OTHER PUBLICATIONS

Jul. 6, 2004 PCT International Search Report in International Application No. PCT/US2004/002757 (8 pages).

(Continued)

*Primary Examiner* — Victor Nguyen
(74) *Attorney, Agent, or Firm* — Alana T. Bergman, Esq.

(57) ABSTRACT

A device for filtering emboli from blood flowing through a lumen defined by the walls of a vessel in a patient's body. The device has a filter element being expandable from a collapsed configuration to an expanded configuration. The filter element includes a material having pores, and the material having pores includes cylindrical wires having at least three different diameters arranged in a pattern of graduated diameters.

28 Claims, 21 Drawing Sheets

U.S. PATENT DOCUMENTS

| | | |
|---|---|---|
| 6,210,500 B1 | 4/2001 | Zurfluh |
| 6,214,026 B1 | 4/2001 | Lepak et al. |
| 6,245,089 B1 | 6/2001 | Daniel et al. |
| 6,277,139 B1 | 8/2001 | Levinson et al. |
| 6,312,407 B1 | 11/2001 | Zadno-Azizi et al. |
| 6,325,815 B1 * | 12/2001 | Kusleika et al. ............... 606/200 |
| 6,336,934 B1 | 1/2002 | Gilson et al. |
| 6,346,116 B1 | 2/2002 | Brooks et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,171 B1 | 5/2002 | Gifford et al. |
| 6,383,196 B1 | 5/2002 | Leslie et al. |
| 6,391,044 B1 | 5/2002 | Yadav et al. |
| 6,409,750 B1 | 6/2002 | Hyodoh et al. |
| 6,425,909 B1 | 7/2002 | Dieck et al. |
| 6,461,370 B1 | 10/2002 | Gray et al. |
| 6,485,501 B1 | 11/2002 | Green |
| 6,494,907 B1 | 12/2002 | Bulver |
| 6,558,405 B1 | 5/2003 | McInnes |
| 6,602,271 B2 | 8/2003 | Adams et al. |
| 6,632,241 B1 | 10/2003 | Hancock et al. |
| 6,656,203 B2 | 12/2003 | Roth et al. |
| 6,740,061 B1 | 5/2004 | Oslund et al. |
| 6,773,448 B2 | 8/2004 | Kusleika et al. |
| 6,786,919 B1 | 9/2004 | Escano et al. |
| 6,792,979 B2 | 9/2004 | Konya et al. |
| 6,969,396 B2 | 11/2005 | Krolik et al. |
| 7,001,425 B2 | 2/2006 | McCullagh et al. |
| 7,220,271 B2 | 5/2007 | Clubb et al. |
| 7,323,001 B2 | 1/2008 | Clubb et al. |
| 2002/0004667 A1 | 1/2002 | Adams et al. |
| 2002/0022858 A1 | 2/2002 | Demond et al. |
| 2002/0042627 A1 | 4/2002 | Brady et al. |
| 2002/0045668 A1 | 4/2002 | Dang et al. |
| 2002/0045916 A1 | 4/2002 | Gray et al. |
| 2002/0055747 A1 | 5/2002 | Cano et al. |
| 2002/0058911 A1 | 5/2002 | Gilson et al. |
| 2002/0058964 A1 | 5/2002 | Addis |
| 2002/0091409 A1 | 7/2002 | Sutton et al. |
| 2002/0107541 A1 | 8/2002 | Vale et al. |
| 2002/0111648 A1 | 8/2002 | Kusleika et al. |
| 2002/0115942 A1 | 8/2002 | Stanford et al. |
| 2002/0128680 A1 | 9/2002 | Pavlovic |
| 2002/0161392 A1 | 10/2002 | Dubrul |
| 2002/0161394 A1 | 10/2002 | Macoviak et al. |
| 2002/0165576 A1 * | 11/2002 | Boyle et al. ............... 606/200 |
| 2002/0188314 A1 | 12/2002 | Anderson et al. |
| 2003/0023264 A1 | 1/2003 | Dieck et al. |
| 2003/0040771 A1 | 2/2003 | Hyodoh et al. |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2004/0082967 A1 | 4/2004 | Broome et al. |
| 2004/0153118 A1 | 8/2004 | Clubb et al. |
| 2004/0153119 A1 | 8/2004 | Kusleika et al. |
| 2004/0215167 A1 | 10/2004 | Belson |
| 2005/0192620 A1 | 9/2005 | Cully et al. |
| 2007/0198051 A1 | 8/2007 | Clubb et al. |

FOREIGN PATENT DOCUMENTS

| | | |
|---|---|---|
| EP | 1 181 900 A2 | 2/2002 |
| EP | 1 226 795 A2 | 7/2002 |
| EP | 1 316 292 A1 | 6/2003 |
| EP | 1 560 544 B1 | 1/2008 |
| WO | WO 94/06372 A1 | 3/1994 |
| WO | WO 96/01591 A1 | 1/1996 |
| WO | WO 97/25002 A1 | 7/1997 |
| WO | WO 98/38920 A1 | 9/1998 |
| WO | WO 98/39053 A1 | 9/1998 |
| WO | WO 99/16382 A2 | 4/1999 |
| WO | WO 00/16705 A1 | 3/2000 |
| WO | WO 00/53119 A1 | 9/2000 |
| WO | WO 00/53120 A1 | 9/2000 |
| WO | WO 00/58964 A1 | 10/2000 |
| WO | WO 00/67670 A1 | 11/2000 |
| WO | WO 01/08595 A1 | 2/2001 |
| WO | WO 01/15629 A1 | 3/2001 |
| WO | WO 01/21100 A1 | 3/2001 |
| WO | WO 01/21246 A1 | 3/2001 |
| WO | WO 01/89413 A2 | 11/2001 |
| WO | WO 02/43595 A2 | 6/2002 |
| WO | WO 02/054988 A2 | 7/2002 |
| WO | WO 02/094111 A2 | 11/2002 |
| WO | WO 2004/066826 A2 | 8/2004 |
| WO | WO 2004/066826 A3 | 8/2004 |
| WO | WO 2004/069098 A2 | 8/2004 |
| WO | WO 2004/069098 A3 | 8/2004 |

OTHER PUBLICATIONS

Jun. 10, 2005 PCT International Search Report in International Application No. PCT/US2004/002756 (15 pages).

Sep. 8, 2004 PCT International Search Report in International Application No. PCT/US2004/002587 (17 pages).

US 6,348,062, 02/2002, Hopkins et al. (withdrawn)

US 6,461,371, 10/2002, McInnes (withdrawn)

\* cited by examiner

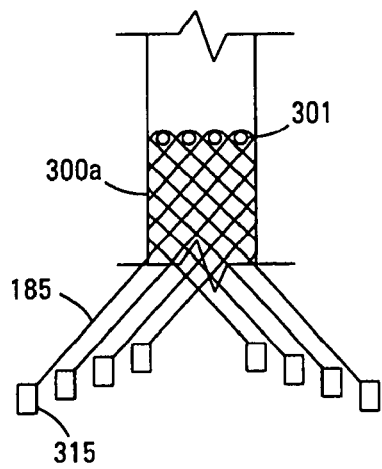
Fig. 15A
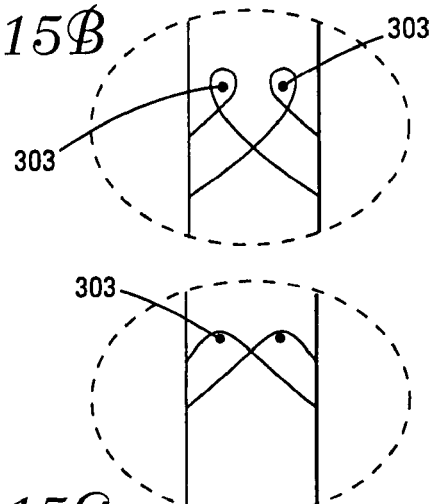
Fig. 15B
Fig. 15C
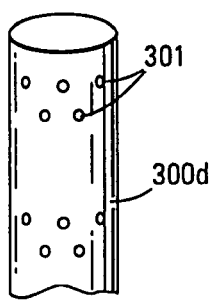
Fig. 15D
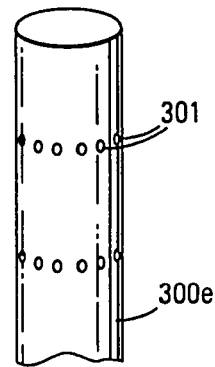
Fig. 15E

EMBOLIC FILTERS WITH CONTROLLED PORE SIZE

CROSS-REFERENCES TO RELATED APPLICATIONS

This application is a continuation of U.S. application Ser. No. 11/704,076, filed Feb. 8, 2007, which is a continuation of U.S. application Ser. No. 10/354,679, filed Jan. 30, 2003, now U.S. Pat. No. 7,323,001 B2, issued Jan. 29, 2008, the contents of each of which are hereby incorporated herein by reference.

FIELD OF THE INVENTION

This invention relates to devices used in a blood vessel or other lumen in a patient's body. In particular, the present invention relates to devices for capturing emboli and particulate in a lumen.

BACKGROUND OF THE INVENTION

During vascular surgery or endovascular treatment of vessels including thrombectomy, atherectomy, balloon angioplasty, and/or stent deployment, debris such as plaque and blood clots can move from the treatment site through a vein or artery and compromise the flow of blood at a location removed from the treatment site. In particular, various protection systems have been developed to prevent such debris from embolizing in the vessel. Distal protection devices include filters and occlusive devices (e.g., balloons) placed distally of the treatment site. Proximal protection devices include filters and occlusive devices placed proximally of the treatment site. In the case of filters, emboli collect within or on the filter. The filter with captured emboli is typically collapsed into a recovery catheter and the catheter withdrawn from the patient's body.

The size or number of emboli that must be retained by the filter in order to prevent clinically undesirable sequaelae is unknown. This uncertainty adds to the complexity of designing a filter with the appropriate characteristics. Small particles might pass through the filter pores and lodge downstream in tissues where they may cause tissue ischemia or tissue necrosis. In the heart, blood can be drawn and measurements can be made to track enzyme levels and determine myocardial damage. However, in the brain there is no easy and inexpensive method to evaluate the effect of a shower of emboli. Within the downstream tissue bed, there is a statistical component to the consequences of an embolus. For example, a 100 micron particle may lodge in a part of the brain where few adverse consequences are detected clinically, or it can lodge in a retinal artery, resulting in blindness in one eye. Therefore, it may be necessary to adjust the filter characteristics to suit the region of emboli filtration. A smaller pore size filter may be needed if protecting the brain than protecting the heart or kidney.

Embolic protection filters permit the passage of blood while retaining emboli that are larger than the pore size of the filter. Filter meshes are commonly made by incorporating holes in a polymer film, by interweaving filaments, or by producing interconnected porosity in a sheet of material (e.g., foam). It is difficult to make an embolic protection filter with the appropriate combination of pore size, pore area, embolic capacity, patency, mechanical strength, low collapsed or retracted profile, and recovery characteristics. Embolic filters made from polymer films commonly have a narrow range of pore sizes but suffer from a low percent open area because there is a limit to how closely the holes can be placed. Too little spacing between holes can result in a weak film that tears upon filter recovery. Foams tend to be bulky, thereby compromising the collapsed profile, and they have low strength.

Interwoven meshes such as braids have the advantage of a pore area which is a high percentage of the total mesh area, excellent strength, and good flexibility, but tend to be made and used in ways that result in a wide range of pore sizes. A wide range of pore sizes is undesirable for a number of reasons. Patency is influenced by pore size. Theoretically, blood can be sheared as it flows through the pore, particularly at the edges of the pore opening. Shearing of blood can activate platelets and initiate a cascade of events that cause blood clotting. When filters are used in the bloodstream, it is common for thrombus to form in the vicinity of the smallest pores and no thrombus to form in the vicinity of the largest pores. Flow through the filter is thereby reduced because part of the filter becomes occluded. In addition, while some filters have a reasonable average pore size, a wide range of pore sizes in these filters may allow large particles to pass through the large pores during either the capture or recovery phase.

A need in the art remains for an embolic protection filter having pores which are both small in size and which do not vary in size beyond an acceptable range.

SUMMARY OF THE INVENTION

The invention provides an embolic filter that is designed to provide the desired characteristics of controlled pore size, high percentage of pore area, high embolic capacity, patency, mechanical strength, low collapsed or retracted profile, and strength during recovery.

It is to be understood that both the foregoing general description and the following detailed description are exemplary and explanatory and are intended to provide further explanation of the invention as claimed.

BRIEF DESCRIPTION OF THE DRAWINGS

FIG. 15A is a schematic illustration of wires winding around a mandrel,

FIGS. 15B and 15C are detailed side views showing the arrangement of the wires on the mandrel, and FIGS. 15D, 15E, and 15F are alternative embodiments of a mandrel suitable for making an embolic protection filter of the invention.

DETAILED DESCRIPTION OF THE PREFERRED EMBODIMENTS

Figure 1A:
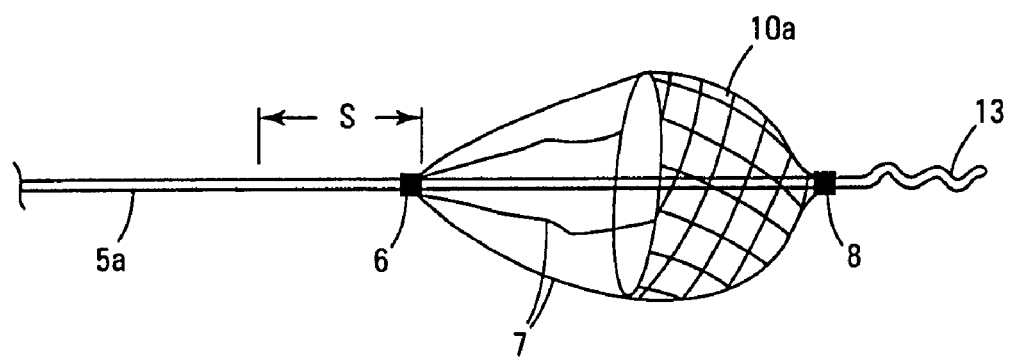
FIGS. 1A and 1B are schematic views of a distal protection system, illustrating expanded and contracted configurations, respectively, of a cup-shaped filter.

The terms "distal" and "proximal" as used herein refer to the relative position of the guidewire, catheters, and filter in a lumen. Thus, "proximal" refers to a location upstream from the "distal" position. That is, the flow of a body fluid, such as blood, moves from the proximal to the distal portions of the device.

The invention encompasses the use of any filtration device to be deployed in a lumen or vessel of a patient. Although the examples relate generally to filter protection devices deployed distal to a treatment site, the device can also be deployed proximal to a treatment site in connection with interrupting or reversing flow through the vessel. In the case of a proximally deployed device, it will be advantageous to construct the device on a hollow elongate member so as to preserve access to the treatment site through the hollow member.

In a preferred embodiment, the distal protection system comprises a catheter which is loaded with an elongate support member or guidewire about which is disposed a distal protection filter. The elongate support member is structurally similar to a traditional guidewire in some respects. However, it is not used as a means of navigating the patient's vascular system and, therefore, does not need to be provided with all of the features of flexibility and steerability as does a traditional guidewire. With these differences in mind, the terms elongate support member and guidewire may be used interchangeably herein. A floppy tip (described further below) may be at the distal end of the elongate support member or guidewire. Typically, the filter is introduced into a blood vessel through an introducing catheter. Methods of introducing guidewires and catheters and the methods for the removal of such devices from vessels are well known in the art of endovascular procedures. In a typical procedure using the device of this invention, the elongate support member and filter are loaded into an introducing sheath or catheter and moved into the vessel and through the catheter to the treatment site. This is done typically by advancing a first, or introduction guidewire, through the vessel to the region of interest. A catheter is advanced over the guidewire to the region of interest, and the guidewire removed. Then the filter or other functional device carried by the elongate support member is advanced down a catheter sheath to the region of interest but within the catheter. The catheter sheath is withdrawn to deploy (expand) the filter at the region of interest. Alternatively, the filter is preloaded into a catheter and held in place by an outer sheath of the catheter and they are together advanced through the vessel to the region of interest without using an initial guidewire. In this embodiment the catheter/filter combination will be used to navigate through the vessel to the region of interest. Then the catheter is withdrawn to deploy the filter. In a second alternative, an introduction guidewire is advanced to the region of interest, and the filter (contained in a catheter) is advanced over the guidewire to the region of interest, at which point the catheter is removed leaving the deployed filter near the region of interest on the guidewire. In this embodiment the filter is not comprised of an elongate support member as previously defined, and the guidewire and/or filter may be configured to preserve a spatial relationship between the guidewire and the filter. For example, the guidewire may be configured to prevent the filter from advancing beyond the distal end of the guidewire.

In other embodiments of the invention, no catheter is required for filter delivery. For example, the filter may be stretched axially so as to reduce its diameter to a size suitable for navigation through a vessel and across a treatment site.

In some embodiments of the invention, the device can include an actuator instead of being self-expanding. Actuators include struts, coaxial elongate elements, expandable elements such as balloons, support frames, etc.

Typical dimensions of a filter used in the devices of this invention range from 2 mm to 90 mm in length, and from about 0.5 mm to 2 mm in diameter before deployment, and from about 2 mm to 30 mm in diameter after deployment. A typical guidewire is about 0.2 to 1.0 mm in diameter and ranges from 50 cm to 320 cm in length.

The components of the distal protection system are made from biocompatible materials. Materials also may be surface treated to produce biocompatibility. The elongate support member may be formed of any material of suitable dimension, and generally comprises metal wire. Suitable materials include stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, and the like. A shape memory or superelastic metal such as nitinol is also suitable. The elongate support member may be solid or may be hollow over some or all of its length.

The material used to make the filter or filter support structure is preferably self-expanding. Suitable materials include metals such as stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, silk, and the like. A shape memory or superelastic metal is particularly suitable for those applications when it is desired for an element, such as a filter, to assume a pre-determined three-dimensional shape or for a guidewire to maintain a pre-determined curvature. A shape memory or superelastic metal comprising nickel and titanium known as "nitinol" is commercially available in various dimensions and is suitable for use as both a guidewire and a filter. For example, nitinol tubular braid can be heat set into a desired shape, compressed for delivery to a site, and then released to resume the heat-set shape.

The filter element has a body defining an interior cavity. The filter body has a plurality of openings or pores such that, when the filter element is in its deployed configuration within the vessel lumen, fluid flows through the filter element and particles of the desired size are captured inside the interior cavity of the filter element.

The filter may comprise any material that is suitably flexible and resilient, such as a mesh, i.e., a material having openings or pores. The filter may comprise braided, knitted, woven, or non-woven fabrics that are capable of filtering particles, preferably having pore sizes from 30 to 500 microns. Woven or non-woven fabrics may additionally be treated to fuse some or all of the fiber intersections. The fabric may be spun or electrospun. Suitable materials include those formed from sheets, films, or sponges, polymeric or metallic, with holes formed by mechanical means such as laser drilling and punching, or by chemical means such as selective dissolution of one or more components. For example, a suitable filter material is braided tubular fabric comprising superelastic nitinol metal. Mesh fabric of nitinol material can be heat-set to a desired shape in its expanded configuration.

The material comprising the filter is preferably at least partially radiopaque. This material can be made radiopaque by plating, or by using core wires, tracer wires, or fillers that have good X-ray absorption characteristics compared to the human body. Radiopaque filters are described in U.S. patent application Ser. No. 10/165,803, filed Jun. 7, 2002, entitled "Radiopaque Distal Embolic Protection Device," the contents of which are hereby incorporated by reference herein.

The embodiments of this invention, described in detail below in connection with the figures, are suitable for use with various distal protection systems that are known in the art. The filter may have a windsock type shape. The construction, deployment and retrieval of a filter having this shape is described, for example, in U.S. Pat. No. 6,325,815 B1 (Kusleika et al.), the contents of which are hereby incorporated by reference herein.

The filter may also be a cup-shaped or basket-shaped device which forms a proximally facing opening when expanded. The construction, deployment, and retrieval of such a filter is described in WO 96/01591 (Mazzocchi et al.). This cup-shaped device may generally resemble an umbrella or a parachute, having a dome-like structure curving radially outwardly from the guidewire or elongate support member. Other shapes may be equally suitable in performing a filtering function, such as a conical shape, or a relatively flat disc shape. The filter may include a filter basket having a self-expanding radial loop designed to position the filter basket within the vasculature and to hold the filter basket open during deployment. Such a filter is described in EP 1 181 900 A2 (Oslund et al.). It will be appreciated that the shape of these filtration devices shown in various embodiments are merely illustrative and are not meant to limit the scope of the invention.

Regardless of the shape of the filter, the filter preferably is deployed using an elongate support member. This can be done in various ways, and one or both of the proximal and distal ends of the filter may be affixed to the elongate support member (by a fixed element) or may be slidably disposed about the elongate support member (by one or more sliding elements).

One type of sliding element comprises inner and outer annular rings. The first ring fits within the second ring. The inner diameter of the first ring is larger than the diameter of the elongate support member so that the sliding element can slide over the elongate support member. The sliding element can be affixed to the filter fabric by placing the fabric between the first and second rings. However, this is not meant to be limiting, and the filter fabric can also be affixed to the sliding element by adhesive, solder, crimping, or other means known in the art. The sliding element may comprise any stiff material such as metal or polymer and preferably the slider is radiopaque. Suitable materials include stainless steel, titanium, platinum, platinum/iridium alloy, gold alloy, polyimide, polyester, polyetheretherketone (PEEK), and the like. Movement of a sliding element with respect to the elongate support member can be facilitated by coating one or both of the inside of the sliding element and the outside of the elongate support member with a friction-reducing coating, such as polytetrafluoroethylene or a lubricious hydrophilic coating.

Fixed elements include annular rings. Also included within this meaning is an element that is crimped, adhered, soldered, or otherwise fastened directly to the elongate support member. Also, the filter fabric may be attached directly to the elongate support member. In any event, the sliding and fixed elements (or any attachment point) typically comprise radiopaque material to assist in the placement of the filter. In addition, one or more radiopaque markers may be positioned at various locations on the protection device. These radiopaque markers or marker bands comprise a material that will be visible to X-rays and they assist in positioning the device.

Some distal protection filters include a floppy tip at a distal portion of the guidewire or elongate support element. The floppy tip provides an atraumatic and radiopaque terminus for the device. An atraumatic tip prevents vessel injury during initial placement or subsequent advancement of the device. A radiopaque tip helps the physician verify suitable tip placement during fluoroscopy. The floppy tip preferably comprises a springy or resilient material, such as a metal (e.g., stainless steel, iron alloys such as Elgiloy™, platinum, gold, tungsten, and shape memory or superelastic metal such as nitinol) or polymer (e.g., polyetheretherketone (PEEK), polyimide, polyester, polytetrafluoroethylene (PTFE), and the like). Springy materials are desirable because they tend to retain their shape. The physician will initially shape the tip, typically with a slight curve, and then as the device is advanced through the body the tip will be deflected as it encounters obstacles. It is desirable, after the inevitable deflections during insertion, that the tip restore itself to the pre-set shape. Polymeric materials additionally may be reinforced with metals or other fillers. The tip may be a monofilament or multifilament (such as a cable). The floppy tip may be tapered or have a uniform diameter over its length. The floppy tip may comprise a tube, or could have circular, flat, or other cross-sections. It may be coiled. The tip may comprise one or more elements (for example, parallel independent structures). The tip may be polymer-coated or otherwise treated to make the surface slippery. The floppy tip can be any desired length.

The filter comprises biocompatible materials such as metals and polymeric materials. Materials such as metals and polymeric materials can be treated to impart biocompatibility by various surface treatments, as known in the art. When wire is used, the wire is selected on the basis of the characteristic desired, i.e., stiffness or flexibility, and the properties can depend upon both the diameter of the wire and its cross-sectional shape. The size, thickness, and composition of elastic materials are selected for their ability to perform as desired as well as their biocompatibility. It is to be understood that these design elements are known to one of skill in the art.

Filters are typically constructed as described in U.S. Pat. No. 6,325,815 B1. See column 3, line 63, to column 4, line 16; and column 4, line 48, to column 5, line 36. The filter body typically comprises a length of a braided tubular fabric, preferably made of nitinol. The filter body is typically made by placing a braided tubular fabric in contact with a molding surface of a molding element which defines the shape of the desired filter body. By heat treating the braided tubular fabric in contact with the molding surface of the molding element, one can create a filter body having virtually any desired shape.

Braiding is a process for producing a tubular interwoven structure from individual strands. Braids are typically produced in continuous lengths on commercially available braiding machines. Some commercial products produced on braiding machines include rope, shoelaces, and reinforcing jackets for electrical cable. Medical products produced by braiding include stents, vascular grafts, and catheter reinforcing layers.

In a typical braiding process for making a 72 stranded braid, lengths of strands, such as wire, are wound onto bobbins. In this example 72 bobbins are wound with wire. Each bobbin is loaded into the carrier of a 72 carrier braiding machine. Typically braiding machines for medical use have from 16 to 144 carriers or more. Each wire is led through a tensioning mechanism in the carrier and all wire strands are gathered at a common central elevated position along the (typically vertical) axis of the braiding machine, where they are fastened to a take-up mechanism. The take-up mechanism may be a long mandrel arranged along the axis of the braiding machine and onto which the braid is formed during the braiding process. Once so configured, the carriers are rotated relative to the axis of the braiding machine. The carriers are rotated in a serpentine path, half of them moving clockwise and the other half moving counterclockwise, so as to interweave the strands in a programmed pattern. While the carriers are rotating, the take-up mechanism advances the woven braid in a direction away from the carriers. The combination of these motions produces a helix of strands twisting in a clockwise direction along the mandrel, interwoven with a helix of strands twisting in a counterclockwise direction along the mandrel. In this manner continuous lengths of braid are produced with an inside diameter of the braid equal to the outside diameter of the braiding mandrel. The individual braid strands, while still on the mandrel, can be twisted together after the length of the mandrel has been braided. If desired, after removing the mandrel from the braiding machine, the strands can be heat-treated. In the case of nitinol strands, heat treatment on the mandrel at about 525° C. for 10 minutes or so can cause the nitinol-braided fabric to remember the shape and size of the mandrel when the nitinol is at rest.

The average pore sizes of filters of the invention preferably range from 30 to 300 microns. In another preferred embodiment, the average pore sizes range from 30 to 150 microns. A pore size of about 120 microns is preferred for devices intended to be used in connection with coronary procedures and a pore size of about 50 microns is preferred for devices intended to be used in connection with carotid or intracranial procedures. The variation in pore size within the filter should be minimized. In preferred embodiments of the invention, the standard deviation of the pore size is less than 20 percent of the average pore size. In other preferred embodiments, the standard deviation of the pore size is less than 15, 10, 5, or 2 percent of the average pore size.

The percent open area of the filters of the invention is preferably greater than 50 percent. In other preferred embodiments, the percent open area is greater than 60, 70, or 80 percent. A standard formula is used to calculate the percent open area of a given design. The percent open area is calculated by dividing the total pore area by the total filter area (including the pore area).

The filters of the invention preferably are made of a material having a tensile strength of greater than 70,000 psi (7031 kg/cm$^2$), more preferably greater than 150,000 psi (14,062 kg/cm$^2$), and more preferably greater than 200,000 psi (17,578 kg/cm$^2$). Cast polymer films have a maximum tensile strength of about 10,000 psi (703 kg/cm$^2$); oriented polymer films have a tensile strength as high as 50,000 psi (3516 kg/cm$^2$), and metal filters typically contain wires having a tensile strength of from 70,000 to 300,000 psi (7031 kg/cm$^2$ to 21,093 kg/cm$^2$).

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent. The material comprising the filter (e.g., mesh or fabric with pores, as described above) is indicated by cross-hatching in some of the figures but is omitted from others for simplicity.

Figure 1B:
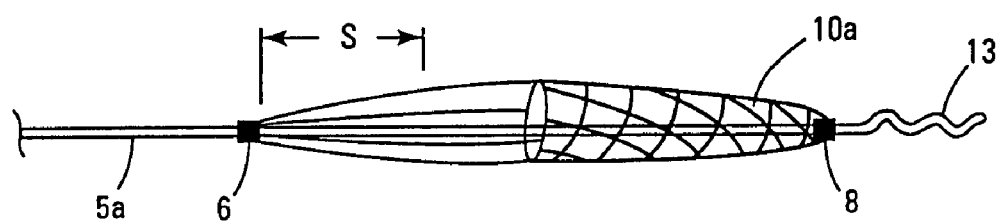
Figure 1C:
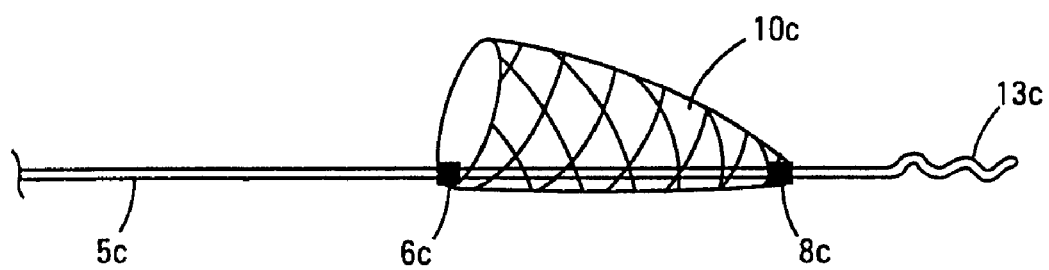
FIG. 1C is a schematic view of an alternative distal protection system having a windsock-shaped filter.

FIGS. 1A, 1B, and 1C illustrate embodiments of various filters in which the concepts of the present invention may be applied. The application of these concepts is not, however, limited to these embodiments and are equally applicable for use in any filter where control of pore size is desirable. FIGS. 1A and 1B illustrate schematic views of a distal protection system in which elongate support member 5a carries filter 10a. The proximal end of the filter is connected to a proximal sliding element 6 and the distal end of the filter is connected to a distal fixed element 8. The distal fixed element is connected at a fixed location on the elongate support member while the proximal slider is configured to slide freely over the elongate support member. Struts or tethers 7 attach to the body of the filter and to sliding element 6. The elongate support member terminates distally at optional atraumatic floppy tip 13. The filter is shown in its expanded deployed configuration in FIG. 1A and in its contracted delivery configuration in FIG. 1B. The figures show that the proximal sliding element 6 travels over the elongate support member a distance S when the filter is contracted to, for example, its delivery configuration.

FIG. 1C illustrates another type of distal protection system in which windsock-shaped filter 10c is attached to elongate support member 5c which terminates at floppy tip 13c. The filter is attached to support member 5c via proximal element 6c and distal element 8c. Either one or both of these elements may be sliding or fixed elements, as described above.

It is to be understood that the following embodiments are useful for any shape or type of filter. For example, these embodiments are useful for any filter deliverable by any manner to a desired position in a body lumen where control of the desired characteristics of the filter as set forth above is desired. In particular, the invention includes both proximal and distal filters.

Minibraid Filters

Figure 2:
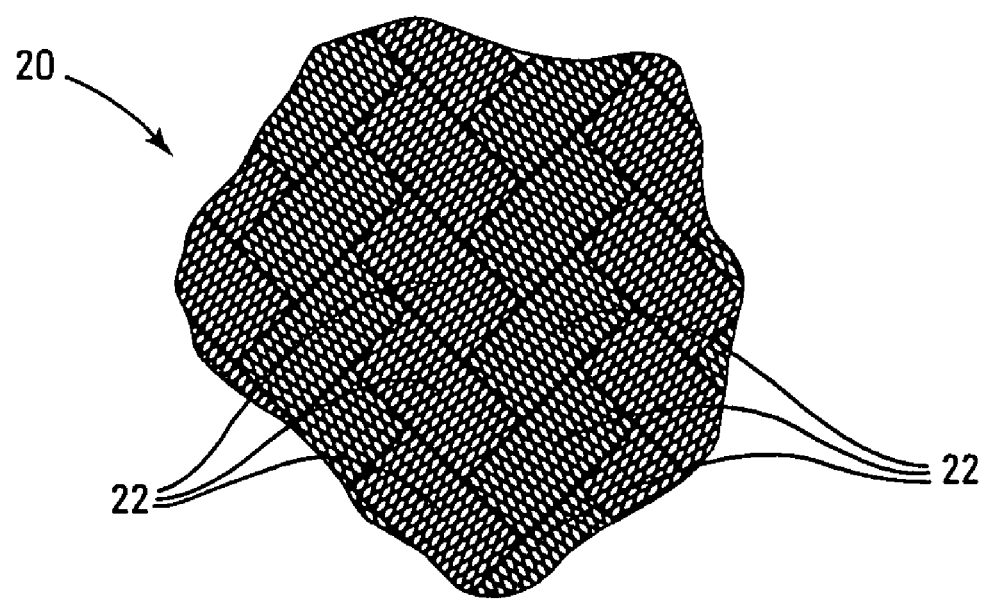
FIG. 2 is an enlarged view of minibraid material used in a filter.

One way to control the pore size and pore distribution in a filter is to use minibraids. FIG. 2 illustrates schematically a self-expanding material 20 used to form a filter of this invention. The self-expanding material 20 comprises braided strands of braided nitinol. Minibraids 22 may be formed from eight strands of nitinol wire (0.001 inch (25 micron) diameter) as described with respect to FIGS. 3A and 3B. Alternatively, minibraids 22 may be formed as described with respect to FIGS. 4A and 4B. It is noted that these minibraids are easier to handle than unbraided wire of this diameter. Twenty-four of these minibraids are braided together to form a second braided, self-expanding material 20, in a 2/2 braid pattern, having 192 filaments. The pore size of this second braid is approximately 100 microns in a 4 mm braid diameter. The braided material shown in FIG. 2 can be used to form a filter similar to the one shown in FIG. 1. In preferred embodiments, the weave of the filter is much tighter (see FIG. 2) than the weave shown in FIG. 1. In the preferred embodiments in which the weave is tight, the pore size and pore distribution are determined almost entirely by the characteristics of the minibraid.

One of skill in the art recognizes that other diameters of wire and other materials can be used to form the minibraids. For example, 0.0007 inch (17.8 micron) diameter nitinol wire is a good choice for forming the braided material shown in FIG. 2. For purposes of this application, a minibraid has a diameter from 0.002 inch (51 micron) to 0.050 inch (1270 micron). In a preferred embodiment, a minibraid has a diameter from 0.005 inch (127 micron) to 0.020 inch (508 micron).

Figure 3A:
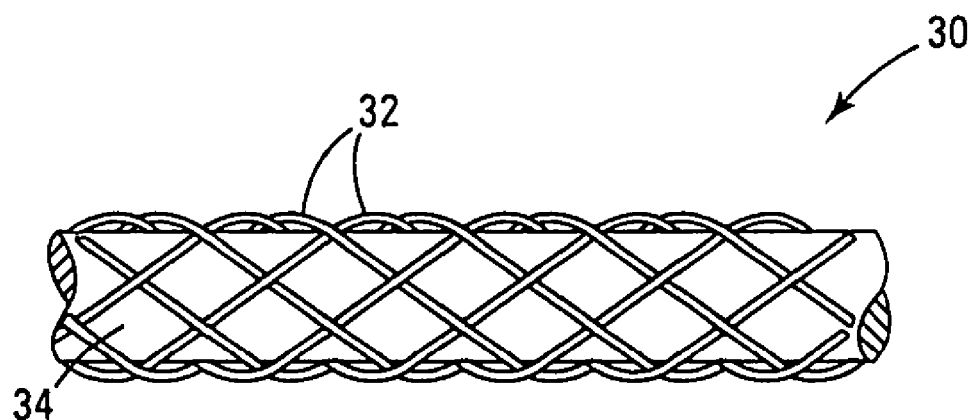
FIGS. 3A and 3B are side views of a minibraid suitable to form the braid material shown in FIG. 2.
Figure 3B:
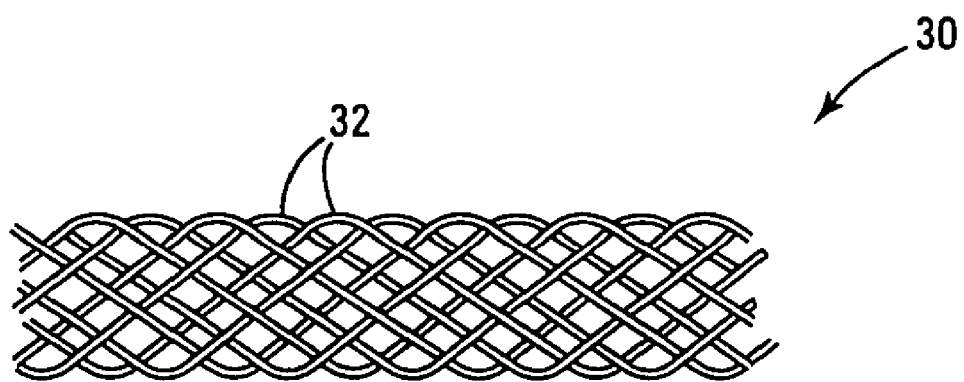

FIG. 3A is a side view of material 30 useful as a minibraid. Material 30 is formed from eight small diameter wires 32 wound around core wire 34. FIG. 3A shows 0.001 inch (25 micron) diameter nitinol wires braided over a 0.005 inch (127 micron) aluminum core wire. This material can be used to form a second braid, described above for FIG. 2, after which the aluminum core wire 34 can be dissolved away. Acid dissolution is preferred because it was found that alkali (NaOH) dissolution caused the nitinol to become embrittled. Core wire 34 alternatively may be a polymeric material, such as polyester, which can be removed by heating. FIG. 3B is a side view showing the shape of material 30 after the core wire has been removed. Alternatively, the core wire can be retained in the minibraid.

Figure 4A:
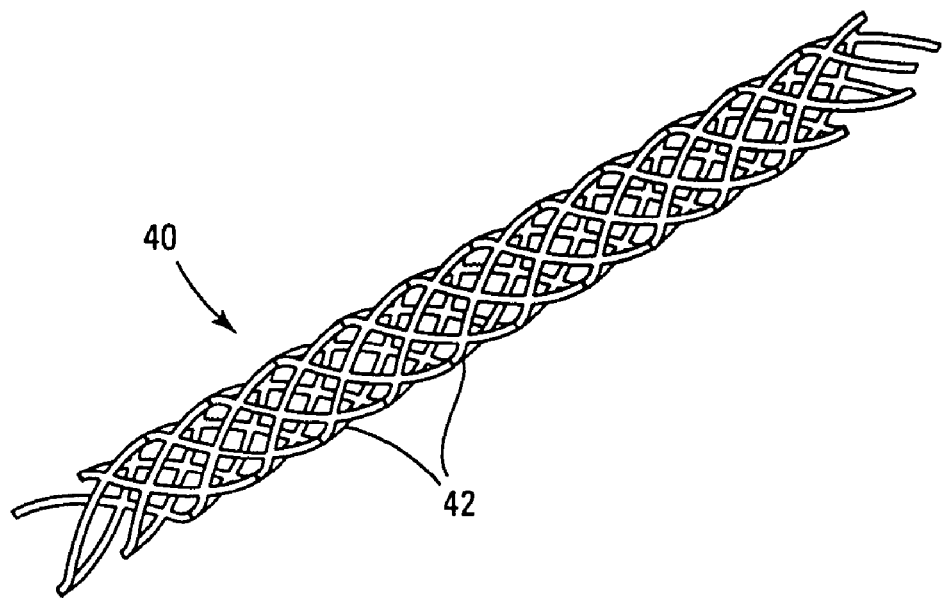
FIGS. 4A and 4B are side views of a minibraid suitable to form the braid material shown in FIG. 2.

FIG. 4A is a side view of material 40, suitable for use as a minibraid. In this embodiment, a tube ranging in diameter from 0.005 inch (127 micron) to 0.020 inch (508 micron) is etched to form material 40, comprising segments 42. In forming the minibraid from material 40, regions of a stainless steel hypotube are masked and then the hypotube is etched using ferric chloride. Laser etching can also be used to form a material of the desired structure.

Figure 4B:
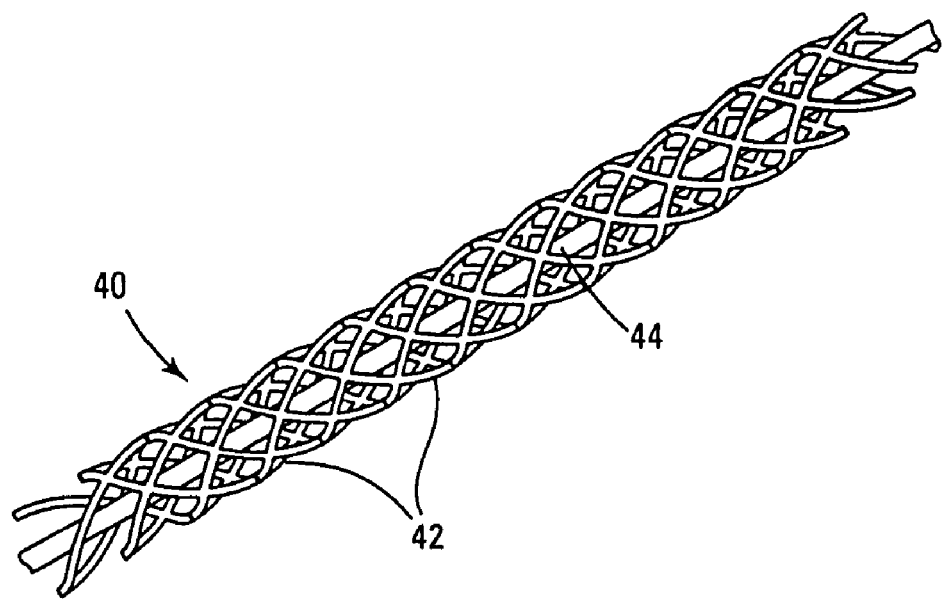

FIG. 4B shows a side view of material 40 in which etching has occurred with core wire 44 added. Material 40 is then braided to form a second braid structure suitable for use in this invention, as shown above in FIG. 2 and as described further below. Core wire 44 prevents material 40 from collapsing under tension during the braiding operation. Core wire 44 can be removed as described above in connection with FIG. 3 or can be retained in the minibraid.

Figure 5A:
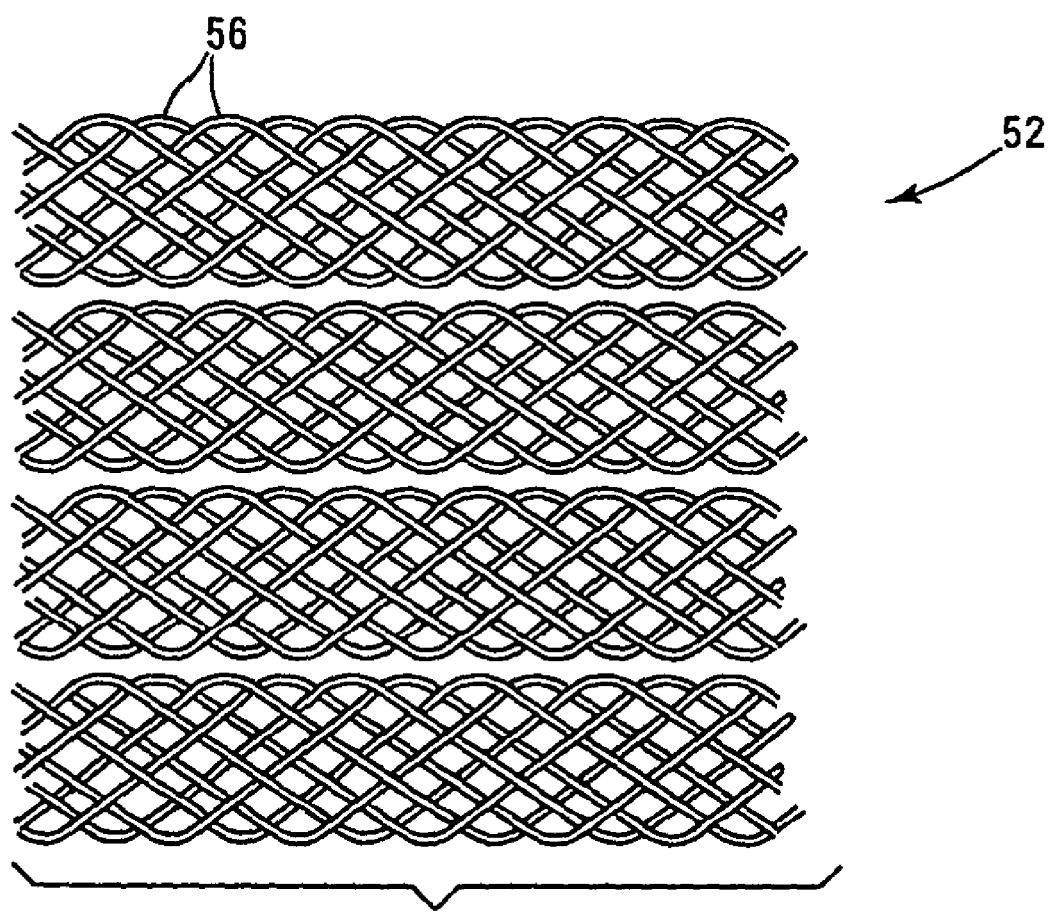
FIG. 5A is a side view of a conical filter formed from minibraid.

FIG. 5A shows a side view of a filter formed from minibraid 52 comprised of 0.001 inch (25 micron) diameter braided nitinol wires 56. The nitinol wires 56 are braided on a core rod 54 of diameter 0.005 inch (127 micron). The minibraid and core rod 54 are then wrapped around a mandrel approximately 4 mm (millimeters) in diameter and the nitinol is heat set on the mandrel by heating to 525° C. for five minutes. If the core is polyester it can be burned off during heat treatment. If the core is aluminum, it can be dissolved away by acid treatment subsequent to the heat treatment. FIG. 5A does not show the core rod 54. The mandrel has a conical shape that forms a suitable filter for the practice of the invention. In any event, the core rod preferably is removed and the resultant conically shaped filter 50, illustrated in schematic perspective view in FIG. 5B, is ready for use.

Figure 5B:
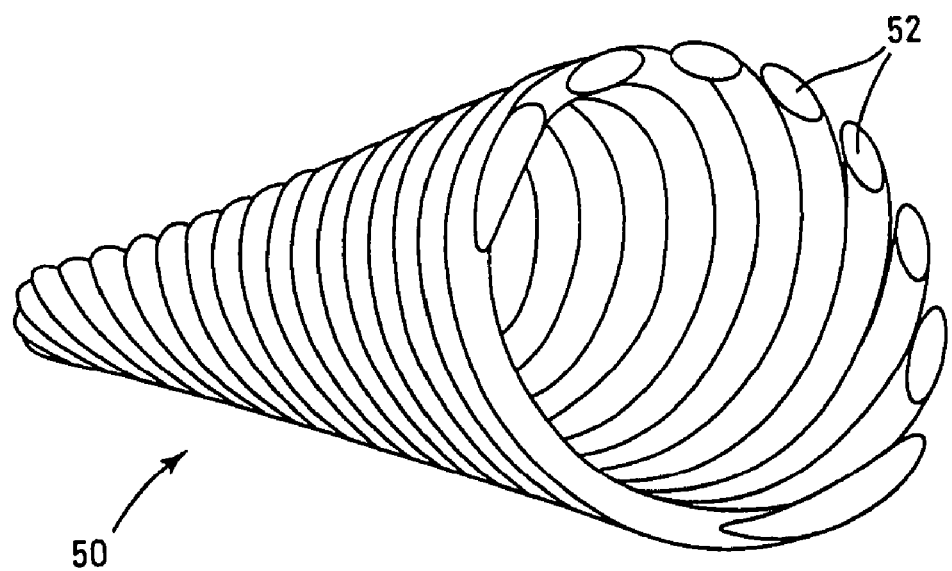
FIG. 5B is an illustrative perspective view of the conical filter of FIG. 5A.

FIG. 5B shows a perspective view of the conically shaped filter 50 formed from minibraids. Optionally, the minibraids can be interwoven with an opposingly wound helix of solid or minibraid filaments to provide additional structural integrity. The pore size and pore distribution are determined almost entirely by the characteristics of the minibraid because the spaces between the minibraids are minimized. The structures shown in FIGS. 3, 4, and 5 can achieve pore sizes comparable to those described in connection with FIG. 2.

Coiled Wire Filters

Figure 6E:
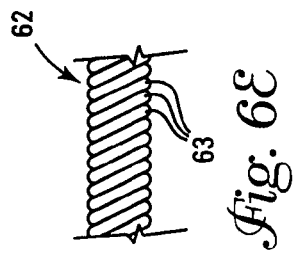
FIG. 6E is a schematic view of a single filament coiled wire.
Figure 6F:
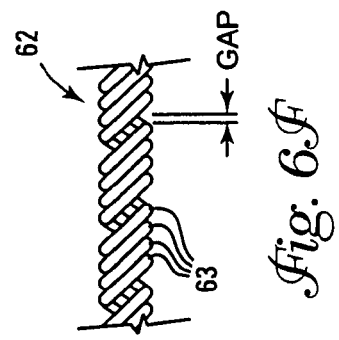
FIG. 6F is a schematic view of a multiple filament coiled wire.
Figure 6B:
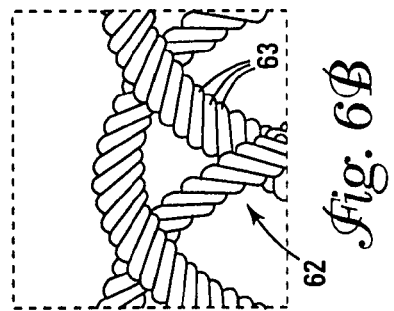
FIG. 6B is an enlarged view of a section of the braid of FIG. 6A.
Figure 6D:
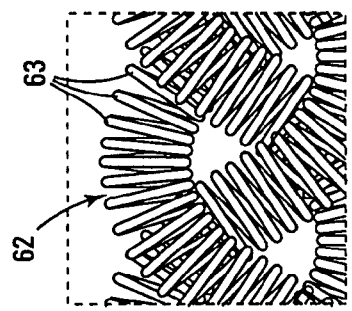
FIG. 6D shows an enlarged view of the braid of FIG. 6C.
Figure 6A:
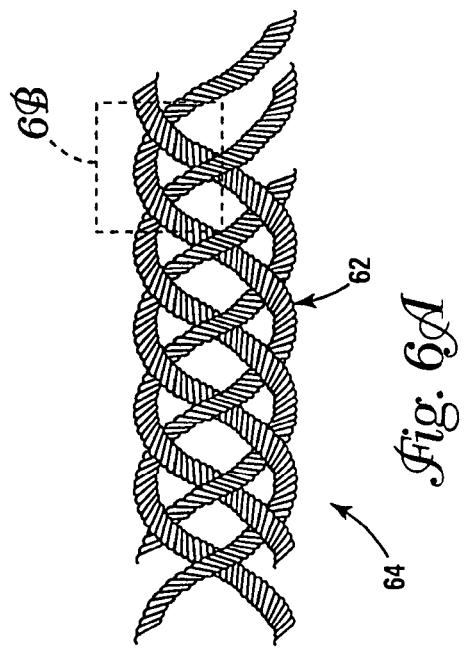
FIG. 6A is a schematic view of a braid comprising coiled wire.
Figure 6C:
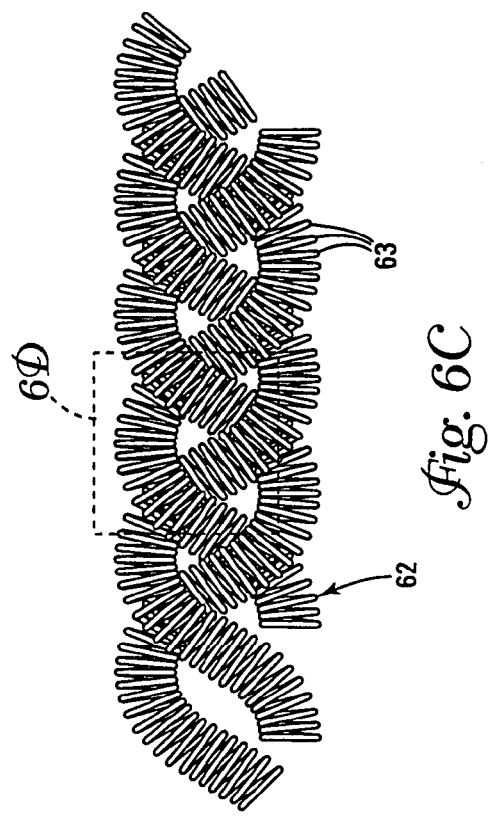
FIG. 6C is a schematic view of a braid having expanded wires.

Another way to control the pore size and pore distribution in a filter is to use coiled wire. FIGS. 6A to 6D illustrate a coiled wire, in which one or more wires 63 are wound around a central axis to produce coiled wire 62. The coiled wire can be formed by twisting wires around a central core or, preferably, by twisting wires without a central core as is commonly done in the wire and cable industry. Although the embodiments shown have the appearance of coils it is understood that suitable structures include helical wound filaments, commonly referred to as stranded wire or cable in the wire and cable industry. This coiled wire is more flexible than a single wire of the same overall diameter. Coiled wire 62 can itself be braided, woven, or wound in a helical pattern to form a suitable filter material, depending upon the desired characteristics. Preferably the coiled wire comprises nitinol, which can be heat set to a desired configuration. FIG. 6A shows braid 64 comprising coiled wires 62, and FIG. 6B is an enlarged view of a section of braid 64. FIG. 6C illustrates coiled wires 62 having coils 63 in an expanded configuration, and FIG. 6D shows an enlarged view of the braid of FIG. 6C. Filters can be made from a single filament coiled wire as shown in FIG. 6E or from multiple filament coiled wire as shown in FIG. 6F. One could achieve pore sizes in the range of 100 microns by braiding 24 coiled wires of 8 strands each followed by expanding the individual coiled wires.

Coiled wire can be formed by coiling or twisting individual strands around a core wire, as described above for minibraids. If the individual strands are nitinol then the strands can be heat set to memorize the shape on the core wire, and the core wire can be removed by means such as acid dissolution. Coiled wire can next be braided with the coiled wire in an unexpanded configuration by tensioning the coils. After braiding, the tension on the coils can be reduced or eliminated by axially compressing the braid, causing the individual wires or strands within the coils to assume their heat set memorized configuration. After the wires expand to their expanded configuration, the average pore size and the pore size distribution are smaller than that of the initially braided structure.

Fenestrated Wire Filters

Figure 7A:
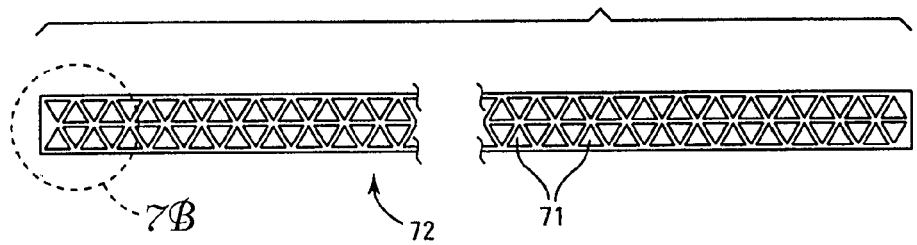
FIG. 7A is a top view of a section of a fenestrated wire.
Figure 7B:
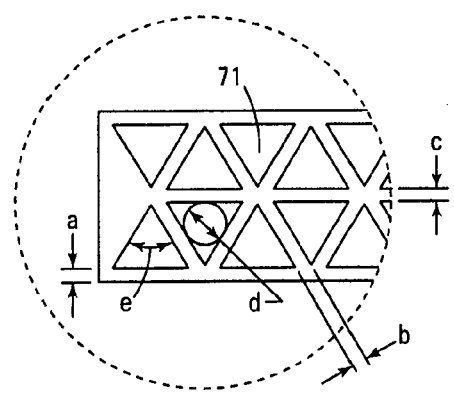
FIG. 7B is a detail view of a portion of the wire of FIG. 7A.
Figure 7C:
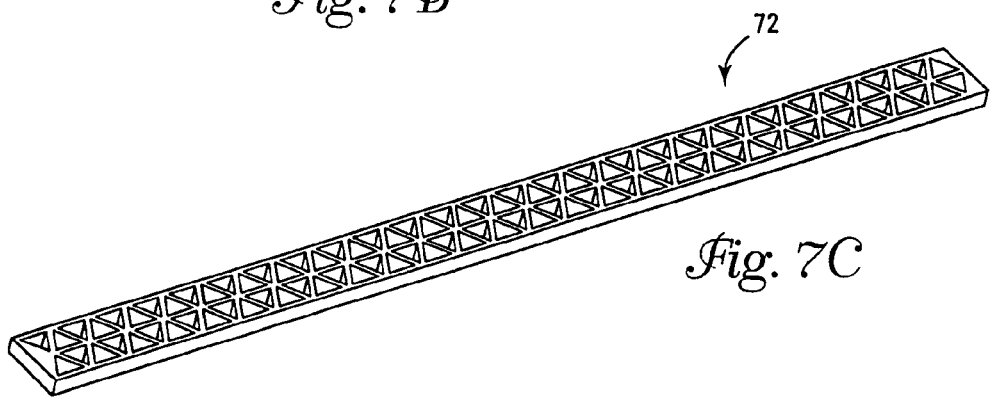
FIG. 7C is a perspective view of the wire of FIG. 7A.

Yet another way to control the pore size and pore distribution in a filter is to use fenestrated wire. FIGS. 7A to 7C illustrate a fenestrated wire, that is, one in which windows have been formed. FIG. 7A shows a top view of wire 72 in which have been formed triangular-shaped windows 71. The windows are spaced uniformly throughout the wire, though one of skill in the art recognizes that the size, shape, and spacing of the windows could be varied to achieve the desired porosity. FIG. 7B is a partial detail view showing the dimensions of the wire (a, b, and c=0.0217 mm) and the windows (d=diameter of 0.0125 mm, e=60°). FIG. 7C is a perspective view of wire 72.

Figure 7D:
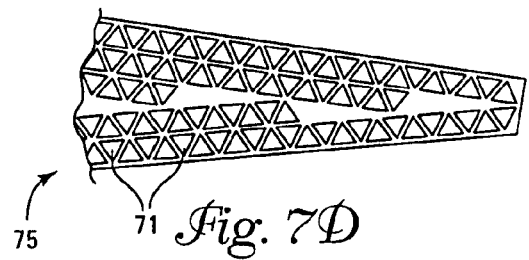
FIG. 7D is a top view of a tapered fenestrated wire.
Figure 7E:
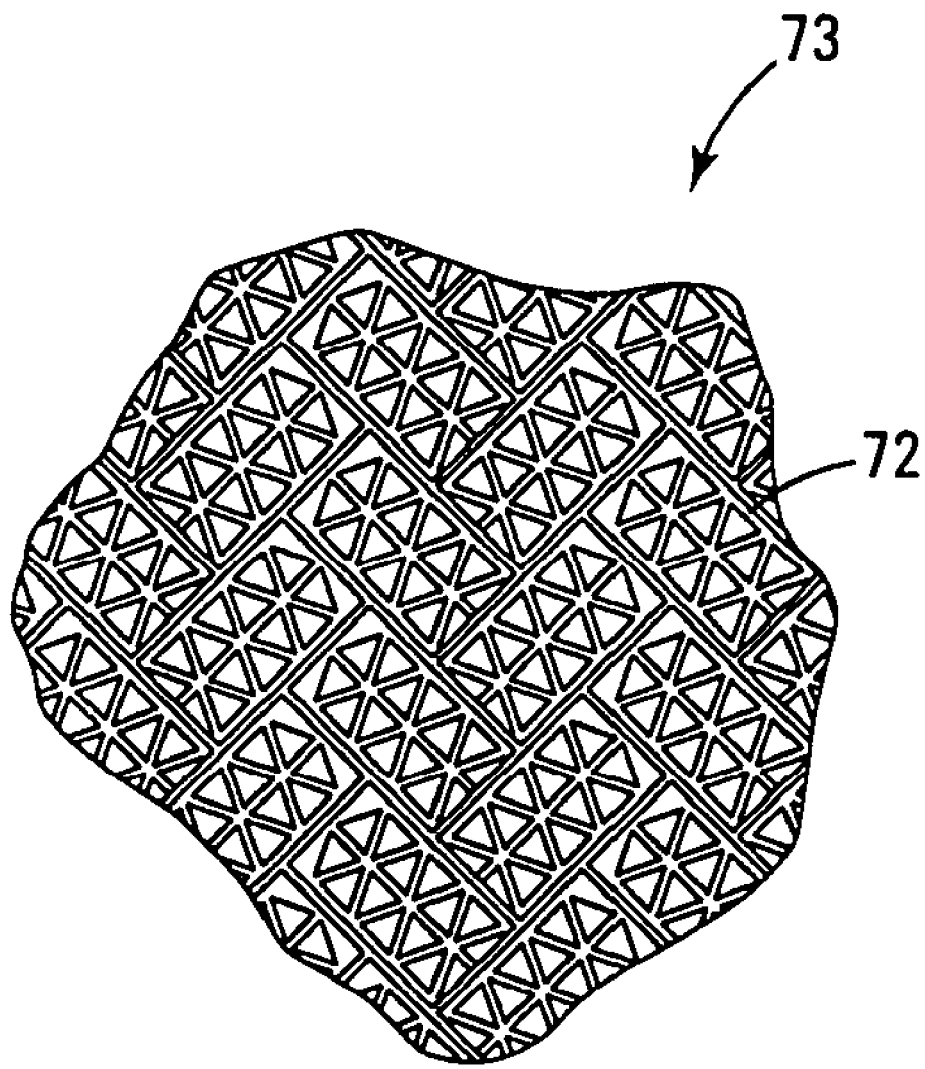
FIG. 7E is an enlarged view of fenestrated wires used in a filter.

FIG. 7D shows fenestrated wires 75 that taper in width. Such tapered fenestrated wires can be braided to form a conical filter. FIG. 7E is an enlarged view of fenestrated wires 72 used in a filter 73. As shown in FIG. 7E, in one preferred embodiment, the space between the individual wires 72 is minimized. In another preferred embodiment, the space between the individual wires 72 is approximately the same as the space within the windows 71 in the fenestrated wires 72. In another preferred embodiment, the space between the individual wires 72 varies from the minimum space possible to approximately the same space within the windows 71 in the fenestrated wires 72.

Fenestrated wire can be formed by masking and etching, laser cutting, rolling using textured rolls, and other methods. Fenestrated wire 72 can be braided, woven, or wound to form a suitable filter material, depending upon the desired characteristics. Ideally the density of the filter structure will be such that the spacing between filter wires is on the order of the size of the fenestrations. In the preferred embodiments in which the weave is tight, the pore size and pore distribution are determined in large part by the characteristics of the fenestrated wire, which has a uniform pore distribution.

Graduated Strand Diameters Filters

Figure 8A:
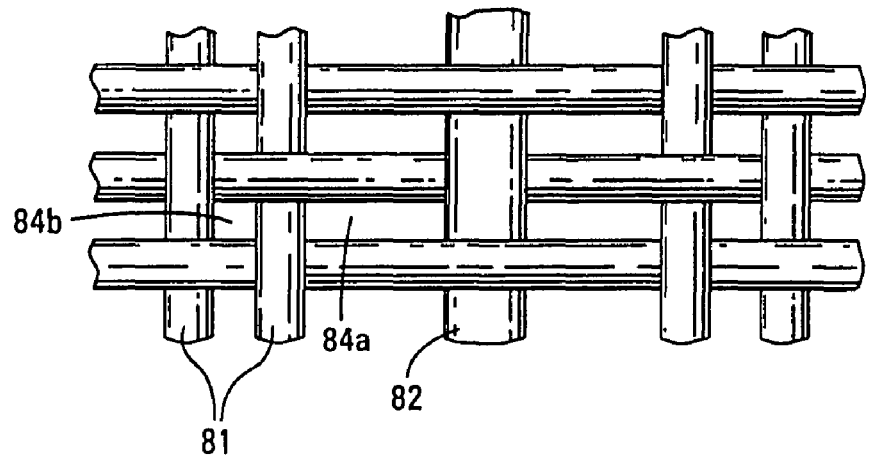
FIGS. 8A and 8B are partial planar views of a woven wire fabric.
Figure 8B:
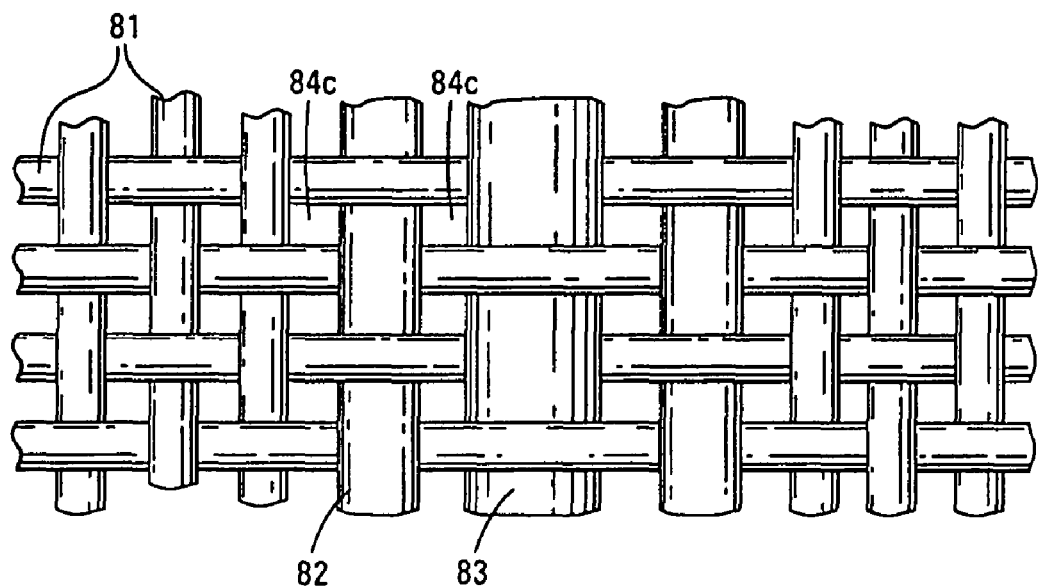

Another way to control the pore size and pore distribution in a filter is to use graduated strand diameters. FIGS. 8A and 8B illustrate woven fabric suitable for use as a filter of this invention, wherein the pore size can be controlled. It has been found that interspersing a number of large diameter strands among smaller diameter strands results in a filter fabric that has a high self-expansion restoring force. That is, the filter assumes the desirable size and configuration during deployment from its compressed and contracted configuration.

To achieve fine pore size filters one can increase the number of individual strands in a mesh, such as a braid, such that they become closely spaced. To prevent excessively large compressed diameters the individual strands must be kept small in diameter. Due to the small strand diameters such filters have poor expansion characteristics despite the large number of individual strands. To overcome this limitation it has been found that good expansion characteristics without excessive bulk can be achieved by interspersing a limited number of large diameter filaments into a mesh of fine filaments. FIG. 8A is a planar view of a section of fabric in which 0.001 inch (25 micron) diameter wire 81, preferably made of nitinol, is woven with a larger diameter wire 82 (0.003 inch (75 micron) diameter), resulting in uneven pore size 84a and 84b in the fabric. Though this embodiment may be useful, a preferred embodiment is one in which wires of varying diameter are woven together to produce uniformly-sized pores 84b. In FIG. 8B, wires 81 of a first diameter (25 micron) are woven together with wires 82 and 83 of two larger diameters (e.g., 50 and 75 micron, respectively). This weave produces pores 84c of uniform size, preferably ranging from 30 to 300 microns. A uniform size is preferred for filtering out particulate and emboli of specific dimensions. The presence of larger diameter wires contributes to an improved restoring force in a filter. That is, the filter expands to the desired structure and size when it is deployed. The disadvantage of making a filter with many large wires can be that, when the fabric is gathered together to form a filter, the diameter of the gathered fabric becomes undesirably large. With this construction, the diameter of the gathered fabric is close to that of fabric comprising only small diameter wire.

Polymer Coated Filters

Figure 9A:
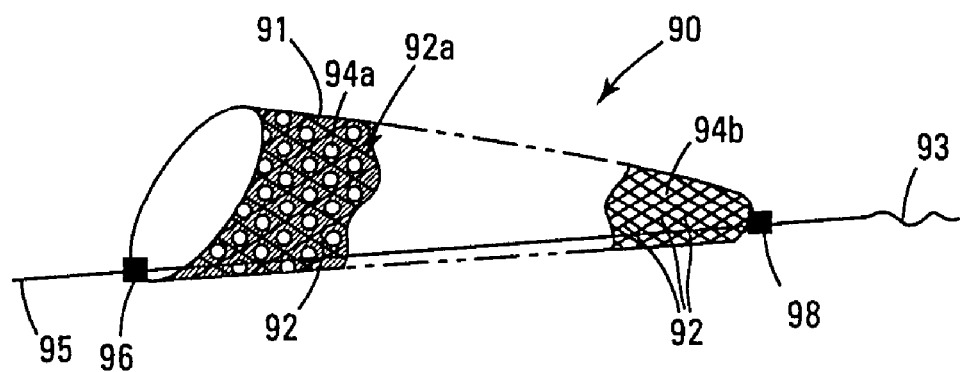
FIGS. 9A and 9B are side views of alternative embodiments of the distal protection filter showing different pore sizes in the filter mesh.
Figure 9B:
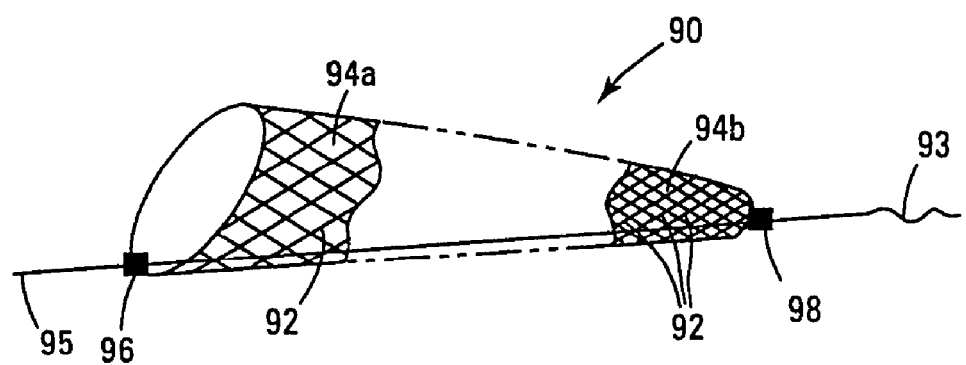

Yet another way to control the pore size and pore size distribution in a filter is to use a polymer coating. FIGS. 9A and 9B illustrate a wire distal protection filter. FIG. 9A has a silicone coating on a portion of it to reduce the pore size of the filter and FIG. 9B is shown with no coating to illustrate the effect of the coating on pore size. Filter 90 comprises wires 92. The filter is disposed about an elongate support member 95, attached by proximal element 96 and distal element 98, and has floppy tip 93. A silicone (such as two part NuSil™ thermoset silicone composition, #MED 10-6640, available from NuSil Technology, Carpinteria, Calif., having an uncured viscosity of about 7000 centipoise and when cured 700% elongation & ultra high tear strength) coating 91 covers a proximal region 92a of filter 90, coating wires 92 of the filter and partially closing the proximal pores 94a. In this manner, the pore size over the length of the filter becomes more uniform, since the large pores of an uncoated filter are made smaller and more similar in size to the pores at the distal end. Preferably, the coating at the more proximal portions of the proximal region 94a reduces a greater percentage of the area of the pores 94a than the more centrally located portions of the proximal region 94a. Such a coating results in a more uniform pore distribution because the more proximal pores are larger than the more centrally located pores in an uncoated filter. It is to be understood that many materials could produce the desired effect, and these include, but are not limited to, other polymers such as polyurethane, latex rubber, thermoplastic elastomers such as those sold under the tradename SANTOPRENE®, available from Advanced Elastomer Systems, Akron, Ohio, butyl or other rubbers, and hydrogels or other expanding polymers. For a typical 72 wire braid of 0.0015 inch (38 micron) diameter wires, a pore size maximum of less than 100 microns with a pore size range of 20 to 100 or less microns should be achievable using this construction. Alternatively, the coating could be applied to the entire length of the wire filter and partially occlude substantially all of the pores, or the coating could be selectively applied to portions of the filter to effect selective pore size reduction.

To produce a coating such as that shown in FIG. 9A, the filter can be dipped in a polymer solution and withdrawn at a programmed rate so as to deposit a film of polymer onto the filter mesh. The filter may be rotated to prevent undesired pooling of the coating. Variables such as % solids content, solvent used, relative humidity, temperature, and others may be controlled to achieve the desired coating properties. A primer may be applied to the mesh, or the mesh may be surface modified, to aid with coating adhesion. To prevent coating migration into the mesh of the filter where a coating is not desired, the filter can be masked with low melting temperature wax or any other masking material as known in the art. The mask is later removed, for example, by heating in the case of a low temperature wax. Alternatively, excess coating can be applied and the excess later removed by means such as laser ablation.

When coatings such as that described in connection with FIG. 9A are applied to woven filamentous structures such as braids, the filament crossings tend to become stiffened since the coating adheres to the filaments in the region of the crossings. In some embodiments filament crossing immobilization is desirable so that pore size uniformity is achieved by preventing lateral or through-thickness migration of filter mesh filaments. In other cases it can be desirable to fracture the coating, particularly at the filament crossings, in order to restore the flexibility of the woven filter structure. Coating fracture can be accomplished by repeated cycling of the coated structure between two filament crossing angles, or alternatively, by embrittling the coating such as by using solvents or by cooling the coating to below its glass transition temperature followed by cycling at least once to fracture the coating.

Coatings applied by dipping can produce a coating of unacceptably large thickness. An applied coating can be ironed to a reduced thickness by pressing the coating between molds prior to solidification of cure of the coating or, in the case of thermoplastic coatings, after the coating has been applied. For example, a conical metal mesh with a thermoplastic coating can be placed inside a heated conical metal mold cavity, and a conical mandrel pressed into the coated conical mesh so as to heat form the coating into a reduced thickness configuration.

Coatings applied by dipping can also produce coatings of an unacceptably large mass. Alternatively, coatings can be applied using vapor deposition techniques. For example, a thermoplastic elastomer can be heated above melting and passed through a spray or atomizing nozzle to produce a mist of molten polymer. The mist of polymer, upon contacting a metal mesh at a temperature below the freezing temperature of the polymer, will condense on and adhere to the metal mesh. By adjusting process parameters, a thin coating can be applied to all or part of the mesh. Alternatively, a polymer can be dissolved into solution and atomized into a mist which is brought into contact with a heated metal mesh. The mist, on contact with the heated metal, will deposit on and adhere to the metal mesh as the heat drives solvent from the mist. Coatings applied using these techniques can be fractured or thinned out using techniques described above.

Elongated Braid Filters

Figure 10A:
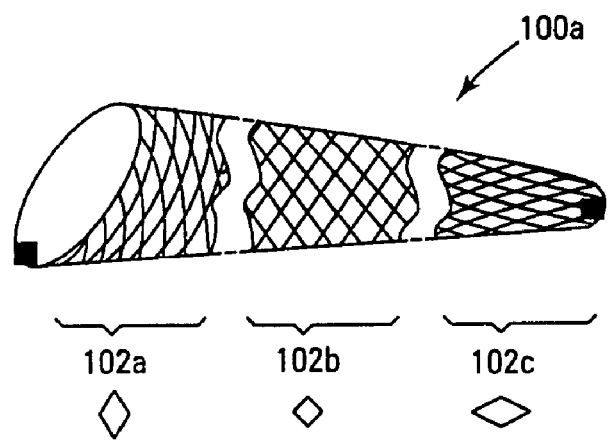
FIGS. 10A and 10C are side views of alternative embodiments of the distal protection filter showing different pore shapes in the filter mesh.

Another way to control the pore size and pore distribution in a filter is to fashion a woven fabric so that pores of the desired sizes or shapes are located in the desired places. FIG. 10A illustrates filter 100a having three regions wherein there are different diamond-shaped pores in regions 102a, 102b and 102c. Region 102a has axially shortened diamonds, region 102b has square diamonds, and region 102c has axially elongated diamonds. These shapes are achieved by stretching a tubular braided structure over a conical mandrel. In this example, a 3.5 mm diameter wire braid of about 100 picks/inch (39 picks/cm) and 72 wires of 0.0015 inch (38 micron) diameter has been stretched over a 4 mm conical mandrel. In use, wall apposition region 102a will contact the walls of the lumen, substantial filtering will begin in region 102b, and emboli will accumulate in capture region 102c. The placement of the area of the square diamonds in the center of the filter results in a lower variation in pore size than placing the square diamonds at the proximal opening of the filter.

Figure 10B:
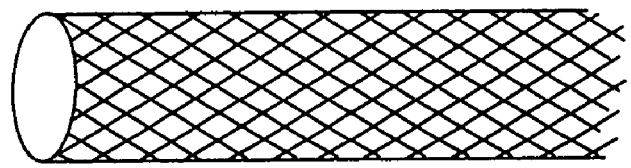
FIG. 10B is a side view of a braid before it is formed into a filter.
Figure 10C:
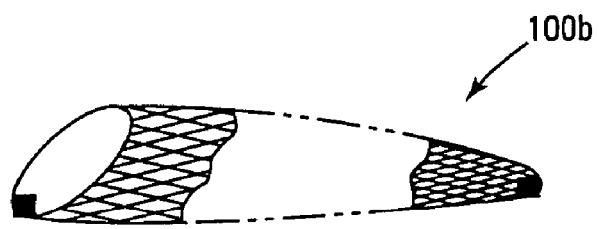

A design shown in FIG. 10C illustrates filter 100b having no square diamonds. In a typical embodiment, a 6 mm diameter braid 100c made from 72 wires of 0.001 inch (25 micron) diameter and about 100 picks/inch (39 picks/cm) (as shown in FIG. 10B) is formed into a filter having a windsock shape with a 4 mm opening (as shown in FIG. 10C). That is, the braid is elongated, thus producing axially elongated diamonds and diameter reduction with consequent reduction in size of the pores. In this example, the maximum pore size, compared to a filter made with similar braid of 4 mm diameter, has been reduced by 8% to 162 microns.

Knitted Mesh Filters

Figure 11A:
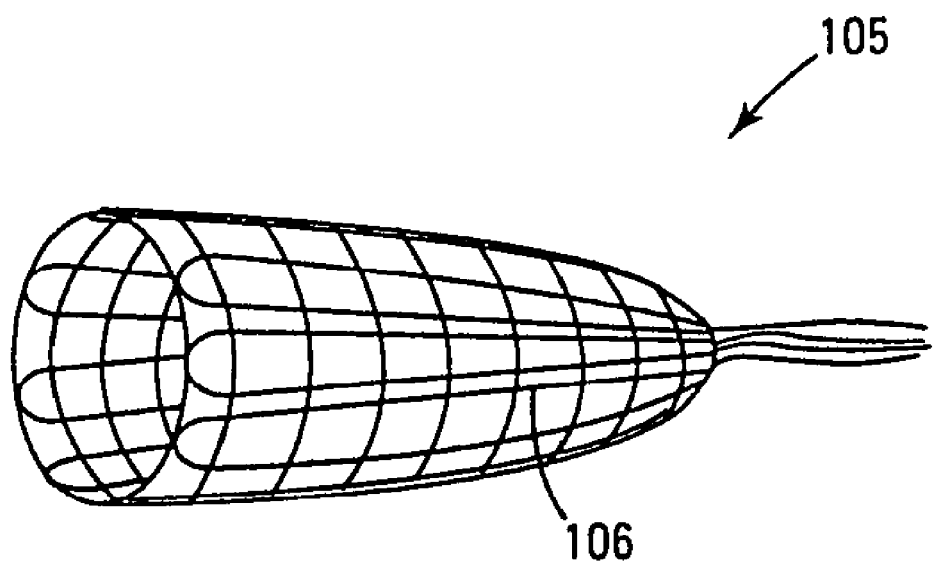
FIG. 11A is a perspective view of an alternative embodiment of a distal protection filter.
Figure 11B:
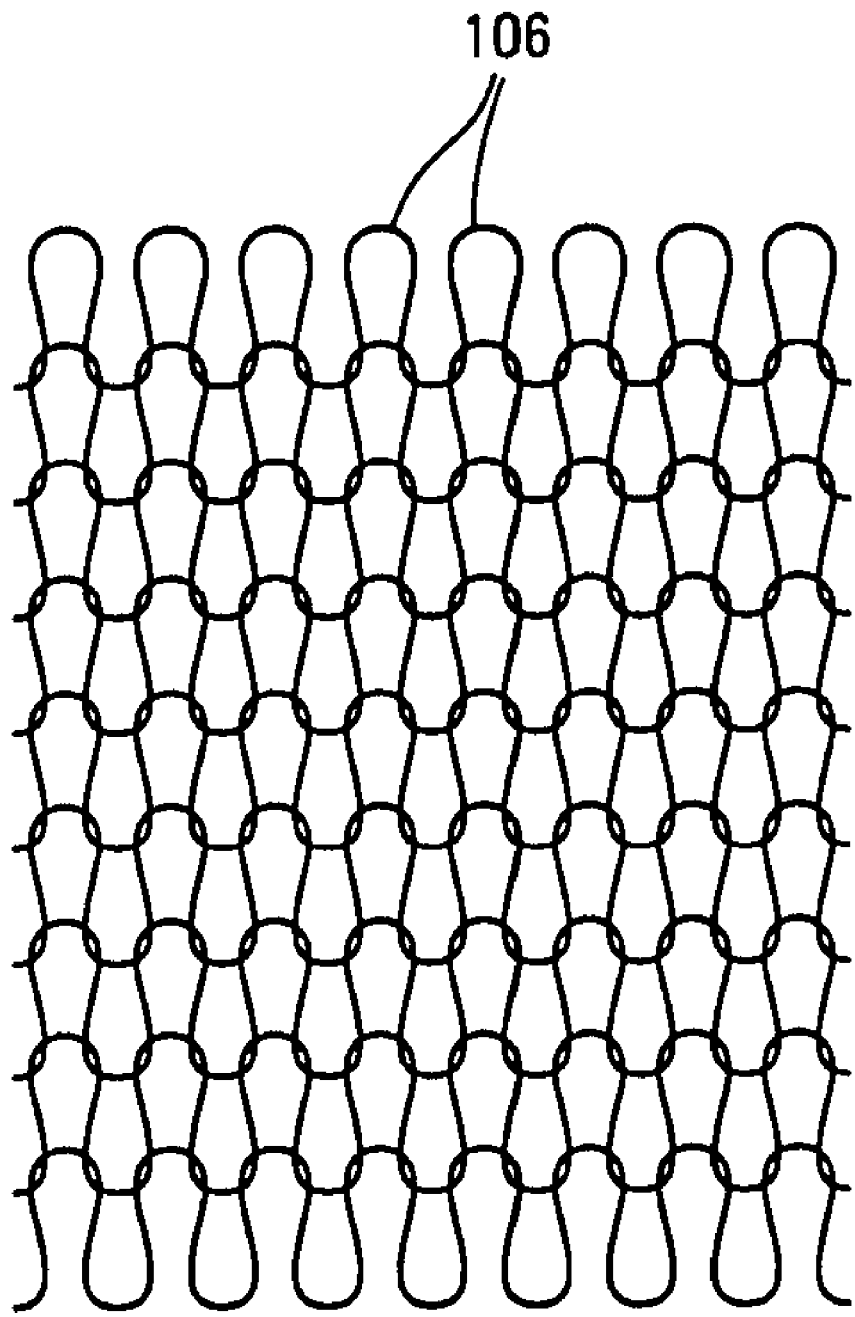
FIG. 11B is a detailed view of a portion of the filter in FIG. 11A.

Another way to control the pore size and pore distribution in a filter is to use a knitted structure, preferably self-expanding nitinol. Knitting is generally defined as a fabric produced by intermeshing loops of yarn, wire, etc. Circular knits and flat knits are preferred. Welt tops may be preferred in some designs. Knitted structures can be made with more pore size uniformity by knitting loops of a predetermined size and using a given number of loops to form a given filter perimeter and a larger number of loops to form a larger perimeter. It is desirable to knit structures close to final geometry so as to minimize manufacturing steps. For example, one could use a circular knitting machine to knit a windsock shape. FIG. 11A illustrates the overall shape of a filter 105 having a knitted structure made of wires 106. FIG. 11B illustrates the mesh in detail and shows how the knitted loops can be interwoven. Preferably, the filter would be knit with no loose ends at the open end by looping the strands back at the edge. The closed end could have loose ends which would be subsequently clamped within a marker band or other structure, or that would be bonded into a unitary structure such as a wire tip.

Ideally this knitted structure would be heat set to assume a self-expanding characteristic. To assist with mesh expansion, it would be desirable to use larger wires for a portion of the knit strands. The large wires would assist in expansion of the knit because the stiffness of the wires increases dramatically with wire diameter. It may be desirable to use progressively changed wire diameters in the knit so as to minimize pore size disruption (similar to the graduated strand diameters filters above). The mesh can be made radiopaque using the same approaches described above.

Filters Made Using Martensitic Braiding or Martensitic Knitting

Figure 12A:
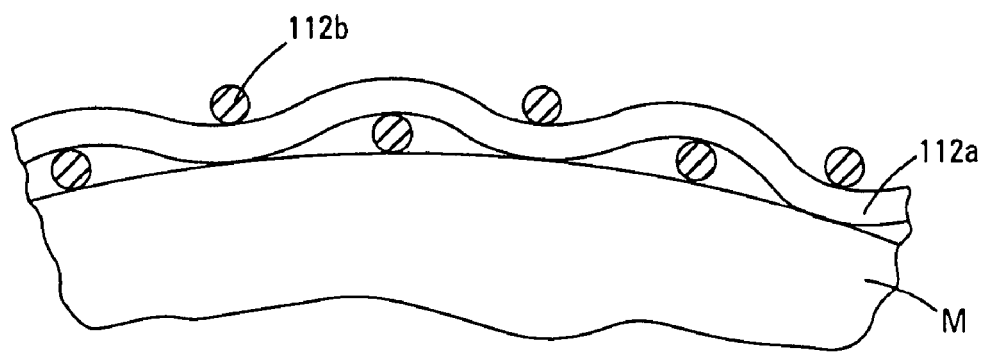
FIGS. 12A and 12B are cross-sectional views showing the arrangement of wires in a braid.
Figure 12B:
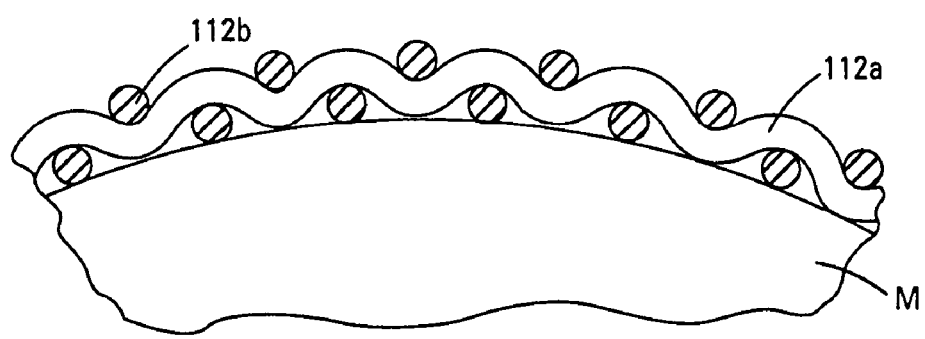
Figure 12C:
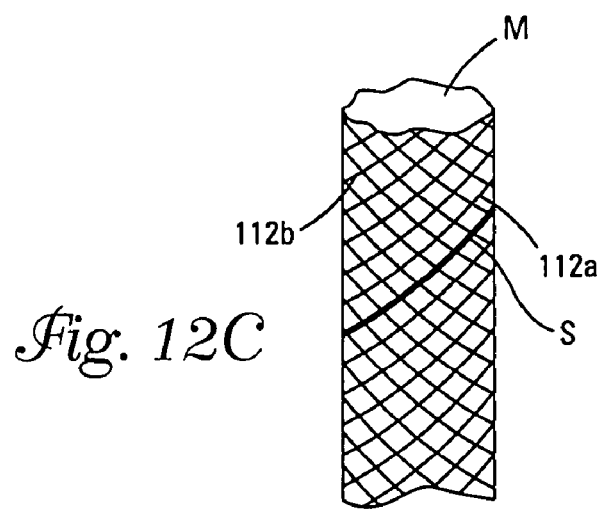
FIG. 12C is a perspective view showing a section line for the views in FIGS. 12A and 12B.

Another way to control the pore size and pore distribution in a filter is to use martensitic braiding. In forming embolic protection filters, it has been found that when braiding high pick count braids (e.g., 200 picks per inch or about 78 picks per cm) the stiffness of the wire limits the ability to achieve high pick counts. This is because the wires weave over and under each other, and the frequency of the curves in the wire increases as the pick count increases. Wire stiffness will limit the achievable pick count to a maximum even if the braiding machine is set to produce a higher number of picks per inch. This is illustrated in FIGS. 12A and 12B, in which a braid formed of wires 112a and 112b has been placed over mandrel M. FIG. 12A shows a low pick count braid, FIG. 12B shows a high pick count braid, and FIG. 12C shows a braid on a mandrel M and a section line S for the views in FIGS. 12A and 12B.

Nitinol wire is very desirable for use in these filters, and it typically is woven at room temperature when in its austenitic phase. For a typical nitinol wire with a ratio of nickel to titanium of 1:1, the martensitic phase can exist when the nitinol is cooled to below about −30° C., although this temperature can be varied substantially depending on the thermomechanical history of the material. The martensitic phase is less stiff, having a modulus of about $5 \times 10^6$ psi, compared to the austenitic phase's modulus of $8 \times 10^6$ psi. ($34.47 \times 10^6$ MPa vs. $55.12 \times 10^6$ MPa). By cooling the nitinol, preferably to below the martensite start temperature, $M_s$, and even more preferably to below the martensite finish temperature, $M_f$, as determined by differential scanning calorimetry at zero stress, higher pick counts can be achieved during braiding because the wires can bend more easily. Such braids, when formed into filters can permit finer filter pore sizes to be achieved.

Similar to martensitic braiding, martensitic knitting can be used to control the pore size and pore distribution in a filter. As discussed above, lowering the temperature of nitinol wire to the martensitic region allows the wires to bend more easily. Wires that bend more easily can be knitted into filters with finer pore sizes.

Filters Made by Wire Removal

Figure 13A:
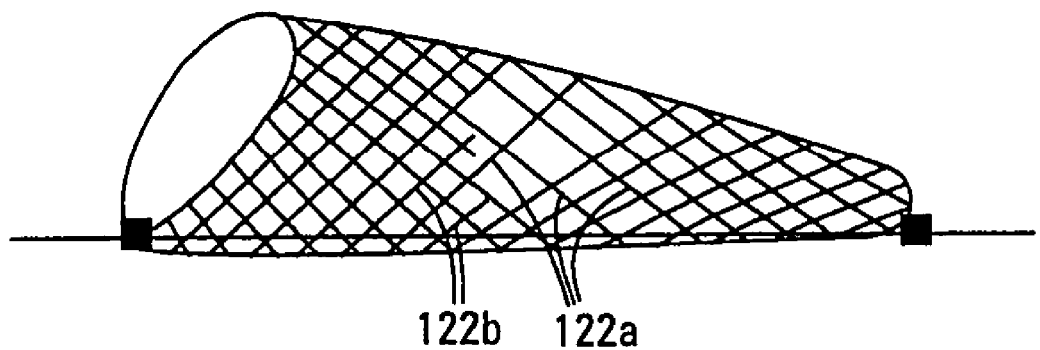
FIGS. 13A and 13B are side views of alternative embodiments of a distal protection filter of the invention.

The pore sizes in embolic protection filters also can be varied by removing portions of the wires comprising the filter. A typical braided filter has smaller pore sizes at its distal end due to its shape. It would be desirable to remove material to make those pores the same size as those at the proximal end. For example, a 72 wire braid could be made with half nitinol and half stainless steel wires. Preferably adjacent strands would alternate between these two materials. After forming the braid into the desired filter shape, a region of the filter at the distal end is placed in a solution that will dissolve the stainless steel wires. For example, a 100 to 300 g/L solution of ferric chloride will dissolve stainless steel and not damage the nitinol. FIG. 13A illustrates a filter 120*a* in which the stainless steel wires 122*b* at the distal end have been removed. Nitinol wires 122*a* remain.

Figure 13B:
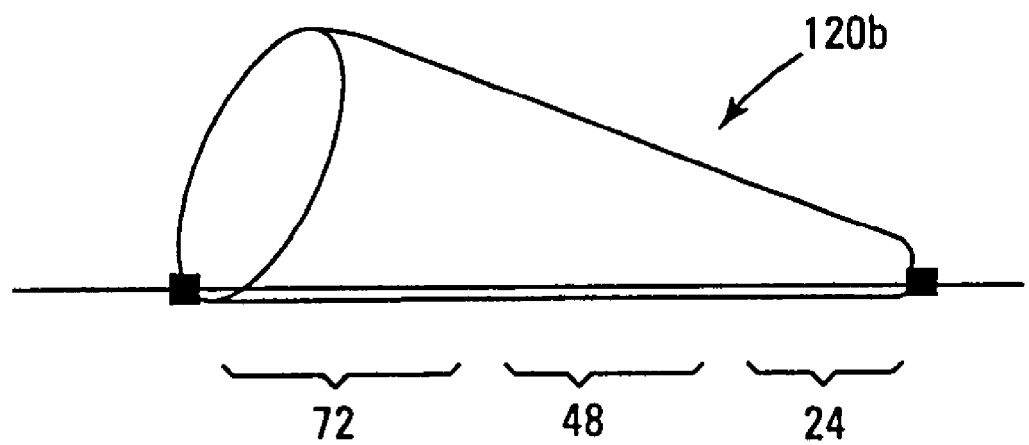

Etching can be combined with various wire compositions to produce a filter such as shown in FIG. 13B, with 72 wires, 48 wires, and 24 wires present in different portions of the filter. For clarity, the individual wires are not shown in FIG. 13B. A 72 wire braid can be made comprising equal parts of nitinol, stainless steel, and gold wire. The braid is made so that the wires alternate within each helix (e.g., nitinol, stainless steel, gold, nitinol, stainless steel, gold, etc.). The braid is removed from the braiding machine and then placed on a mandrel and heat set into a desired filter shape, such as a windsock shape. The proximal element or band is crimped and swaged around the gathered braid, but the distal element or marker is not permanently attached at this time. The filter is then passivated in nitric acid solution to remove nickel from the nitinol surface and to leave a corrosion resistant oxidized titanium surface. Optionally, the proximal one-third of the filter can be masked with wax or other suitable impervious material that can later be removed easily.

The distal two-thirds of the filter is then immersed in a solution of potassium iodide in iodine to dissolve the gold wire. A 20% sodium cyanide solution containing a small amount of hydrogen peroxide is also suitable for this purpose.

The proximal two thirds of the filter then is masked, and the distal one-third of the filter is immersed in ferric chloride solution to dissolve the stainless steel. The mask material is then removed, for example, by heating, and the entire structure is again passivated in nitric acid solution. The distal marker or element is then affixed to the 24 nitinol strands remaining at the distal end of the filter.

It is preferred to use larger diameter nitinol wires than are typically used in such filters in order to produce a filter having sufficient self-expansion properties. The nitinol has to overcome resistance to expansion by the non-shape-set stainless steel and gold wires. For example, for a windsock-shaped filter having a 4 mm opening, 0.002 inch (50 micron) nitinol wires, and 0.001 inch (25 micron) diameter stainless steel and gold wires are suitable for use in this filter.

One of skill in the art recognizes that other wire combinations can be used to form filters similar to those described in FIGS. 13A and 13B. Also, wires can be removed by methods other than by chemical etching. For example, laser cutting, plasma etching, mechanical cutting, water jet cutting, and selective embrittlement followed by fracture are all techniques that would permit removal of a desired portion of wire or wires.

It also may be desirable to remove only a portion of a wire in a region to create a more uniform pore size or an altered pore size distribution. That is, material could be partially removed or etched by the methods described above, thus increasing the pore size in a region. The converse is also true, where material could be added to fine diameter wires such as by sputtering or other physical vapor deposition methods, by plating, or by coating with various polymers, as described above.

A method to remove metal wire by etching is to immerse the filter lengthwise (i.e., the braid formed into its filter shape) and to withdraw it slowly from an etchant bath so that the distal end of the filter remains in the bath the longest. Material removal can be accelerated by flowing etchant over the filter, or to otherwise agitate the etchant. The filter material can be flexed and moved during etching to assure that all wire, even at wire cross-overs, will be exposed to etchant.

Filters Made by Adding Wires During Braiding

Figure 14:
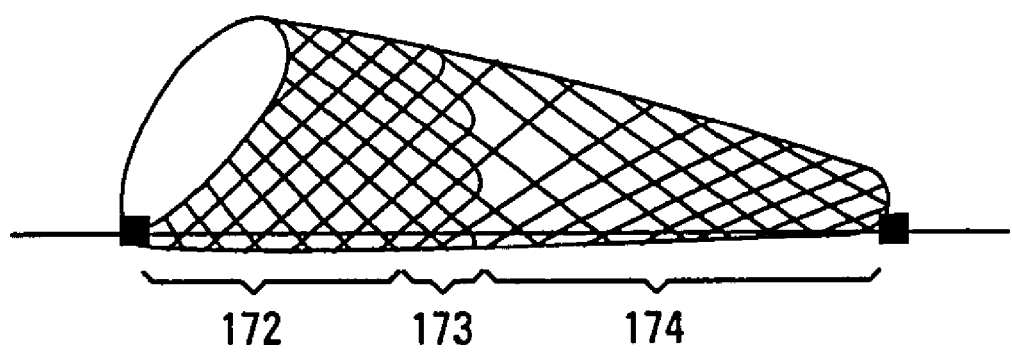
FIG. 14 is a side view of an alternative embodiment of a distal protection filter wherein the pore size is controlled by adding wires during braiding.

Yet another way to control the pore size and pore distribution in a filter is to add wires during braiding. FIG. 14 illustrates a windsock-shaped filter 170 in which the mesh fabric of the filter is braided so that there are fewer wires, as measured around the perimeter, at the distal end 174 than at the proximal end 172 of the filter. This design results in a more uniform pore size. To do this, a length of braid is made, and then the braiding machine is stopped and more wires are added to the braiding machine. The wire ends are looped though the existing braid. The machine is then restarted and the braiding continues to make a suitable length of braid. The filter is formed so that the portion of the braid having the smaller number of wires forms the distal end of the filter. There is a transition region, denoted by 173, between the proximal and distal portions of the filter.

To form a suitable filter, the following procedure can be used: (a) on a 48 carrier braiding machine, load 24 bobbins into alternate carriers, 12 for the clockwise rotation carriers and 12 for the counter-clockwise rotation carriers; (b) braid a desired length of 24 wire braid on the 48 carrier braider; (c) separately, cut 12 lengths of wire and wind one end of each length onto a bobbin such that the wire is wound onto two bobbins; (d) mount one of these bobbins onto a clockwise carrier, loop the other bobbin through the braid tent, through a cell formed by wire crossings, mount the second bobbin onto a counter-clockwise carrier, and remove any slack from the wire by tensioning the carrier; (e) repeat for the other 11 lengths of wire; and (f) continue braiding on the 48 carrier braiding machine.

Clearly, this procedure could be repeated so as to produce a braid with several zones, each having more wires than the previous one. It is also possible to intersperse the additional wires in step (d) above at different heights in the braid tent. This would produce a more gradual transition between zones of wires.

Figure 15F:
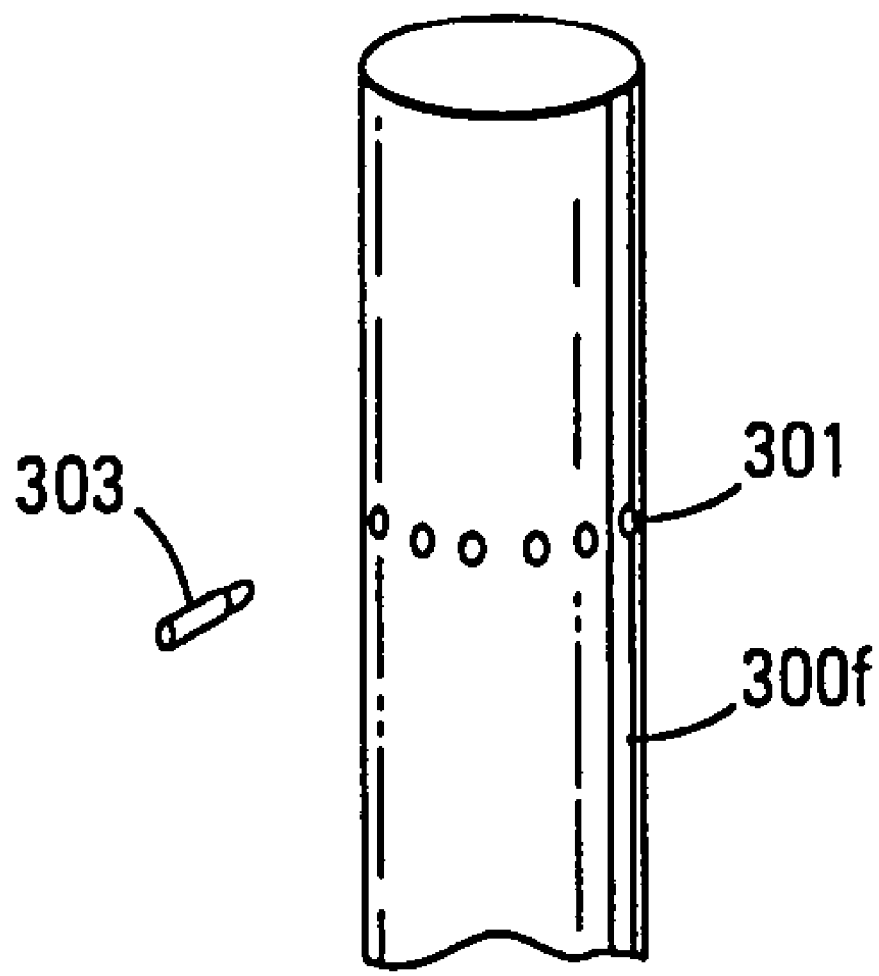

Alternatively, the braiding mandrel can be modified, as shown in FIG. 15F. Mandrel 300*f* in FIG. 15F is shown with pin-receiving holes 301. Pins 303 can be placed in the desired positions so that a braid of the desired wire density and pattern is formed. Braid is braided on the braiding machine until the braid reaches the location of the holes 301 on the mandrel 300*f*. Pins 303 are then inserted into the holes and braid wires are added as described above except that the wires are looped over the pins rather than being looped through the braid tent. Braiding then continues to form the desired length.

It would also be desirable to reduce the number of loose wire ends in a length of braid. These ends can irritate, cut, or puncture vessels and result in damage. FIG. 15A is a schematic illustration showing wires 185 leading from carriers 315. The wires wrap around mandrel 300*a*. To eliminate ends, wires can be mounted on the braiding mandrel by looping the wires over pins 303, mounted in pin-receiving holes 301, as shown in detail in FIGS. 15B and 15C in two alternative patterns. Once all wires are looped and the tension of the carriers adjusted braid can be produced in a conventional way.

FIG. 15E shows a mandrel 300e modified to comprise pin-receiving holes 301 that accept pins in two axial positions. To use this mandrel braid is looped over the first row of pins as described at 15F. Braiding is carried out until the braid length formed on the mandrel reaches the second row of holes. More wires are looped over the second row of pins and braiding recommences until a structure of the desired length has been fabricated. It will be recognized that multiple groupings of pins are possible, for example, see FIG. 15D.

Electroformed Filters

Figure 16:
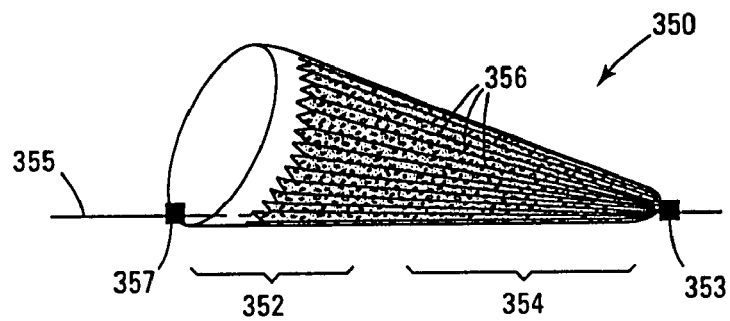
FIG. 16 is a perspective view of an electroformed filter.

Another way to control the pore size and pore distribution in a filter is to form the filters by electroforming. Electroforming can be used to make mesh filters for use in the present invention. Electroforming permits the selection of the pore sizes and distribution of pores. Electroformed mesh films are commercially available from Buckbee-Mears in various pore sizes. Such films may not be as flexible as materials comprising braids, knits, weaves, and the like, but the films can be made very thin or with preferential fold lines, thereby overcoming their flexibility limitations. Such films also can be pleated to assist in the collapse of a filter made from electroformed film. These films may require the support of a secondary frame, either a separate structure or an integral structure, to provide the film with sufficient mechanical integrity to act as an embolic protection filter. Such films can be made into the desired three-dimensional shape by forming onto a substrate, such as a cone-shaped or a dome-shaped mandrel. The films can be formed on a flat substrate and the desired three-dimensional shape can be added by post-processing. Alternatively, the films can be formed directly on the three-dimensional substrate. FIG. 16 shows a perspective view of an electroformed filter 350 having a smooth cylindrical proximal portion 352 and a pleated distal portion 354 having holes 356 to allow the flow of fluid. The filter 350 is disposed about an elongate support member 355, attached by proximal element 357 and distal element 353.

A process for making an electroformed filter could be as follows. First, choose a substrate material, typically nickel or stainless steel, preferably passivated, or metallized ceramic such as indium tin oxide on glass. Second, coat the substrate with photoresist. Third, deposit a pattern for the filter, typically chrome on glass. Fourth, through contact or non-contact methods, print the pattern onto the substrate and expose the photoresist to light through the pattern. Photoresists can be positive action (these are removed in the exposed areas) or negative action (these remain in the exposed area). Fifth, develop the photoresist in a suitable developer; excess photoresist is removed and one is left with a conductive substrate with a photoresist pattern thereon. Sixth, electroplate the substrate with the metal of interest. Typically, an aqueous solution of metal salt is the source of the electroplated metal. Useful metal salts include those of gold, nickel, or platinum. Seventh, remove the patterned photoresist to free the electroformed part from the substrate.

Filter Formed into Mandrel

The following process could be used to form filters for use as embolic protection devices that have a narrow distribution of pore sizes. A form, typically a mandrel, is etched (another suitable process such as laser removal of the mandrel surface can be used) with the filter pattern desired. The mandrel material is removed to some depth under the intended filter surface. Material removal depth can be varied for various portions of the filter.

Next, material is embedded into the grooves/fissures/depressions/etc. in the form surface. In the case of metals, the form can be filled by electroforming metal onto the form surface, by filling the form texture with powdered metal followed by sintering or other agglomeration methods, by metal injection molding, by swaging or otherwise mechanically compressing material into the texture, by using shock waves such as those created by explosives, or by using electromagnetic energy. For polymer filters the form texture can be filled using dipping, casting, thermoforming, or other methods.

Figure 17A:
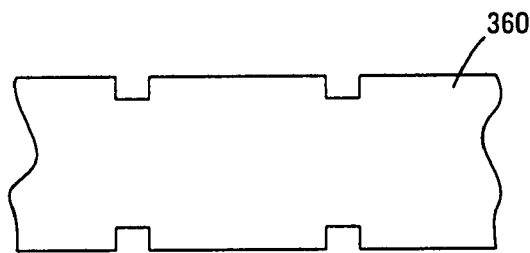
FIGS. 17A to 17C are cross-sectional views of a mandrel and a filter material formed into the mandrel in a process for forming a filter into a mandrel.
Figure 17B:
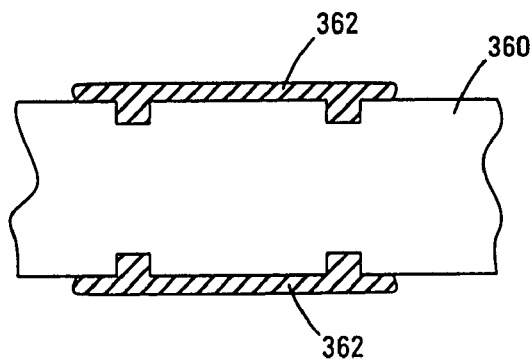
Figure 17C:
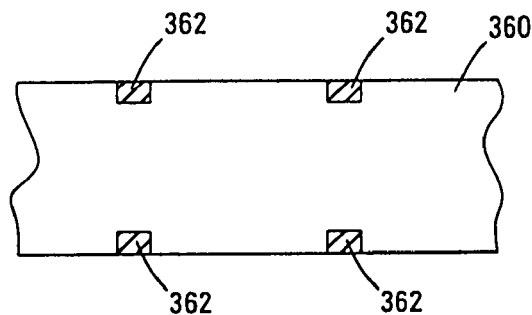

It is expected that excess material will be present above the surface of the mandrel after the material is embedded into the form. Excess material is removed form the form, typically by grinding, leaving a filled form in the pattern of the desired filter. The form can then be removed, typically by dissolving it or melting it out. FIGS. 17A to 17C are cross-sectional views of a mandrel and a filter material formed into the mandrel in a process for forming a filter into a mandrel. FIG. 17A is a cross-sectional view of a mandrel 360. FIG. 17B shows the filter material 362 deposited onto the mandrel 360. FIG. 17C shows the filter material 362 on the mandrel 360 after the excess filter material is removed.

In addition to the methods described above, the pore sizes of the filters described above can also be controlled by the methods described in U.S. patent application Ser. No. 10/354,829, filed Jan. 30, 2003 and entitled "Embolic Filters Having Multiple Layers and Controlled Pore Size", the contents of which are hereby incorporated by reference herein.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

The invention claimed is:

1. A device for filtering emboli from blood flowing through a lumen defined by the walls of a vessel in a patient's body, comprising:
a filter element being expandable from a collapsed configuration to an expanded configuration, wherein the filter element comprises a woven mesh having pores, the woven mesh comprising cylindrical wires having at least three different diameters, and the cylindrical wires having at least three different diameters being interwoven together in at least a portion of the mesh; further comprising an elongate support member and the filter element being carried on a portion of the elongate support member; wherein the diameter of the middle diameter wire is halfway between the diameter of the largest diameter wire and the diameter of the smallest diameter wire.

2. The device of claim 1, wherein the wires are arranged in a graduated diameters pattern from the smallest diameter wire to the largest diameter wire.

3. The device of claim 1, wherein the mesh comprises cylindrical wires having just three different diameters.

4. The device of claim 3, wherein the middle diameter wire is positioned between the smallest diameter wire and the largest diameter wire.

5. The device of claim 1, wherein the mesh is self-expanding.

6. The device of claim 1, wherein when the filter element is in the expanded configuration, the average pore size is from 30 to 300 microns.

7. The device of claim 6, wherein when the filter element is in the expanded configuration, a standard deviation of the pore size is less than 20 percent of the average pore size.

8. The device of claim 1, wherein when the filter element is in the expanded configuration, the average pore size is from 30 to 150 microns.

9. The device of claim 1, wherein when the filter element is in the expanded configuration, the average pore size is from 100 to 140 microns.

10. The device of claim 1, wherein when the filter element is in the expanded configuration, the average pore size is from 40 to 70 microns.

11. The device of claim 1, wherein when the filter element is in the expanded configuration, a standard deviation of the pore size is less than 20 percent of the average pore size.

12. The device of claim 1, wherein when the filter element is in the expanded configuration, a standard deviation of the pore size is less than 15 percent of the average pore size.

13. The device of claim 1, wherein when the filter element is in the expanded configuration, a standard deviation of the pore size is less than 10 percent of the average pore size.

14. The device of claim 1, wherein when the filter element is in the expanded configuration, a standard deviation of the pore size is less than 5 percent of the average pore size.

15. The device of claim 1, wherein when the filter element is in the expanded configuration, a standard deviation of the pore size is less than 2 percent of the average pore size.

16. The device of claim 1, wherein when the filter element is in the expanded configuration, the filter element has a percent open area greater than 50 percent.

17. The device of claim 1, wherein when the filter element is in the expanded configuration, the filter element has a percent open area greater than 60 percent.

18. The device of claim 1, wherein when the filter element is in the expanded configuration, the filter element has a percent open area greater than 70 percent.

19. The device of claim 1, wherein when the filter element is in the expanded configuration, the filter element has a percent open area greater than 80 percent.

20. The device of claim 1, wherein the mesh has a tensile strength greater than 70,000 psi.

21. The device of claim 1, wherein the mesh has a tensile strength greater than 100,000 psi.

22. The device of claim 1, wherein the mesh has a tensile strength greater than 200,000 psi.

23. The device of claim 1, wherein the mesh is made of metal.

24. The device of claim 1, wherein the mesh is made of nitinol.

25. The device of claim 1, wherein the filter element has proximal and distal portions, the filter element having a shape in the expanded configuration which defines a cavity having a proximal facing opening.

26. The device of claim 1, wherein the mesh was made by braiding.

27. The device of claim 1, wherein the mesh was made by knitting.

28. The device of claim 1, wherein the diameter of the largest diameter wire is up to three times the diameter of the smallest diameter wire.

* * * * *